(12) United States Patent
Kumar et al.

(10) Patent No.: US 11,428,664 B2
(45) Date of Patent: Aug. 30, 2022

(54) DEVICE AND METHOD FOR DETECTION OF HAEMOGLOBIN AND ITS COMPLEXES

(71) Applicant: INDIAN INSTITUTE OF SCIENCE, Bangalore (IN)

(72) Inventors: Vinay Kumar, Bangalore (IN); Navakanta Bhat, Bangalore (IN)

(73) Assignee: Indian Institute of Science, Bangalore (IN)

( * ) Notice: Subject to any disclaimer, the term of this patent is extended or adjusted under 35 U.S.C. 154(b) by 512 days.

(21) Appl. No.: 15/509,447

(22) PCT Filed: Sep. 7, 2015

(86) PCT No.: PCT/IB2015/056832
§ 371 (c)(1),
(2) Date: Mar. 7, 2017

(87) PCT Pub. No.: WO2016/038526
PCT Pub. Date: Mar. 17, 2016

(65) Prior Publication Data
US 2017/0241945 A1    Aug. 24, 2017

(30) Foreign Application Priority Data
Sep. 8, 2014  (IN) ............................ 4375/CHE/2014

(51) Int. Cl.
*G01N 27/416* (2006.01)
*G01N 33/72* (2006.01)
(52) U.S. Cl.
CPC ....... *G01N 27/4168* (2013.01); *G01N 33/721* (2013.01)
(58) Field of Classification Search
CPC .......... C12Q 1/00; C12Q 1/001; C12Q 1/004; C12Q 1/005; C12Q 1/006;
(Continued)

(56) References Cited

U.S. PATENT DOCUMENTS

2003/0226769 A1* 12/2003 Sode .................... G01N 33/723
                                              204/403.14
2004/0054267 A1   3/2004 Feldman et al.
(Continued)

FOREIGN PATENT DOCUMENTS

CN          1710418 A   * 12/2005

OTHER PUBLICATIONS

I. Taniguchi, Analysis of Biological Functions of Metalloproteins Using Biocompatible Modified Electrodes, Analytical Sciences, vol. 17, p. i355-i358 (2001).*
(Continued)

*Primary Examiner* — Maris R Kessel
(74) *Attorney, Agent, or Firm* — Meunier Carlin & Curfman LLC

(57) ABSTRACT

An electrochemically active device is provided for collecting and retaining a blood sample with at least a two-electrode member connected to conductive tracks. A receptor with an integral receptor-membrane arranged on the two-electrode member, to receive non-electrochemically active heamoglobin bioanalyte and its complexes from red blood cells (RBC) of said blood sample, through a lysing agent and convert the non-electrochemically active heamoglobin bioanalyte and its complexes, into an electrochemically active bioanalyte and its electrochemically active complexes. The present invention also provides a point-of-care biosensor incorporated with the device of the present invention and method of measuring for the detection and quantitative measurement of concentrations of haemoglobin (Hb), glycated haemoglobin (GHb), methaemoglobin (MetHb) and myoglobin, in reduced volumes of blood samples, by determining redox current values in the reduced volumes of blood samples.

21 Claims, 31 Drawing Sheets

(58) Field of Classification Search
CPC ........ C12Q 1/26–32; C12Q 1/34; C12Q 1/54; G01N 27/48; G01N 27/26; G01N 27/327–3274; G01N 27/4168; G01N 33/487; G01N 33/49; G01N 33/72–726; G01N 27/3277; A61B 5/14532; A61B 5/14535; A61B 5/14536; A61B 5/1477; A61B 5/726; A61B 2562/0295
See application file for complete search history.

(56) References Cited

U.S. PATENT DOCUMENTS

| | | |
|---|---|---|
| 2009/0304547 A1 | 12/2009 | Werner et al. |
| 2011/0127172 A1 | 6/2011 | Liaw et al. |
| 2012/0261257 A1 | 10/2012 | Vanjari et al. |

OTHER PUBLICATIONS

Machine Translation of Cai CN1710418A, Espacenet, last accessed Sep. 23, 2019, pp. 1-9.*

B. Ye, et al, Direct Electrochemistry of Hemoglobin at a Bare Silver Electrode Promoted by Cetyl Pyridinium Chloride and Its Application in Analysis, Electroanlysis, vol. 8, No. 12, pp. 1165-1168 (1995) (Year: 1995).*

B. K. Patel, et al., Deciphering the role of the head group of cationic surfactants in their binding interactions with heme protein and their release by β-cyclodextrin New J. Chem., vol. 42, pp. 14914-14925 (2018).*

G. Li, et al., Imidazole modified silver electrode and its application to the investigation of the electrochemistry of cytochrome c, Analytics Chimica Acta, vol. 319, pp. 275-276 (1996) (Year: 1996).*

F. Viola et al., Native Horse Heart Cytochrome c and to Its Carboxymethylated Derivative: A Comparative Study, J. of Inorganic Biochemistry, vol. 62, pp. 213-222 (1996) (Year: 1996).*

J. Wei, et al, Direct Wiring of Cytochrome c's Heme Unit to an Electrode: Electrochemical Studies, J. Am. Chem. Soc., vol. 124, pp. 9591-9599 (2002) (Year: 2002).*

D. G. Davis, et al., Cyclic Voltammetry of Some Iron Porphyrin Complexes, vol. 38, No. 2, Anal. Chem., pp. 179-183 (1966) (Year: 1966).*

International Search Report and Written Opinion, Application PCT/IB2015/056832, completed Dec. 16, 2015, 11 pages.

* cited by examiner

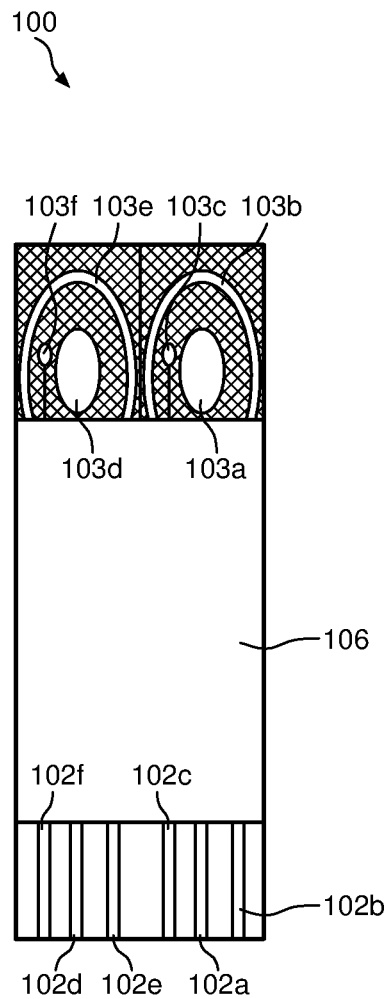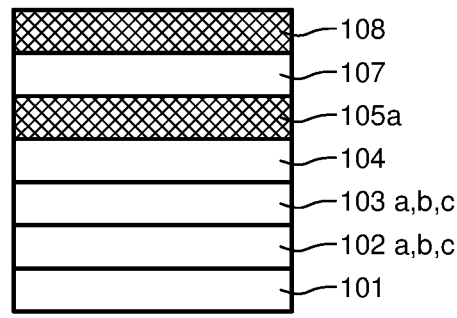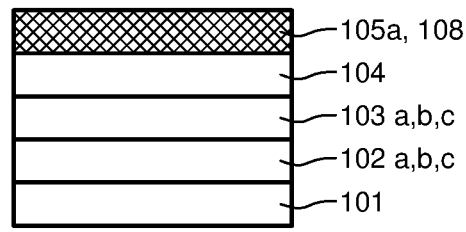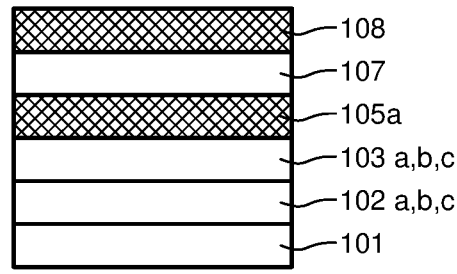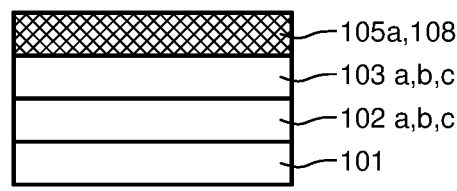
FIG. 7a
FIG. 7b
FIG. 7c
FIG. 7d
FIG. 7e

DEVICE AND METHOD FOR DETECTION OF HAEMOGLOBIN AND ITS COMPLEXES

FIELD OF INVENTION

This invention generally relates to biosensors and methods for quantitative measurement of bioanalytes in biological samples. More particularly, the present invention relates to an electrochemically active biosensor, for converting non-electrochemically active heamoglobin bioanalyte and its complexes in reduced volume of blood samples, into electrochemically active bioanalyte and complexes, for an accurate detection and quantitative measurement of haemoglobin, glycated haemoglobin (GHb), methaemoglobin and myoglobin.

BACKGROUND OF THE INVENTION

Oxygen is most versatile reagent in nature for many different functions in human body. Oxygen is much more soluble in nonpolar than polar solvents. Simple diffusion will not deliver dioxygen fast enough to internal cells in multicellular organism; therefore carriers like haemoglobin and myoglobin are needed. Haemoglobin is the oxygen carrier protein in human body.

Haemoglobin is a globular soluble protein with quaternary structure, which contains four iron ($Fe^{+2}$) atoms in the form of heme prosthetic group. The Direct electrochemical detection of haemoglobin is difficult. Heme iron center is embedded inside the globin chain and it is very difficult for the molecule to communicate at the electrode surface. Haemoglobin is an oxygen transporting metalloprotein inside the RBC, with molecular weight 64,500 dalton. Different forms of haemoglobin exist inside the human body such as Oxyhaemoglobin, deoxyhaemoglobin, methaemoglobin, carboxyl haemoglobin, sulfhaemoglobin etc. Oxyhaemoglobin and deoxyhaemoglobin can bind and transport the oxygen molecule while other forms of haemoglobin cannot bind the oxygen.

Diabetes mellitus has become a major health problem worldwide in many developing countries as well as in minority groups in the developed world. According to International diabetes federation, 382 million people are diabetic worldwide and projections suggest that 592 million people will have diabetes by the year 2035. The majority of the 382 million people with diabetes are aged between 40 and 59 year and 80% of them live in low and middle-income countries. All types of diabetes are on the increase, type 2 diabetes in particular: the number of people with diabetes will increase by 55% by 2035. An additional 21 million cases of high blood glucose in pregnancy are estimated to contribute to the global burden of diabetes. In human as well as financial terms, the burden of diabetes is enormous, provoking 5.1 million deaths and taking up some USD 548 billion dollars in health spending (11% of the total spent worldwide) in 2013.

Type-2 diabetes mellitus is associated with increased cardiovascular and overall mortality. Epidemiological data suggest that classic cardiovascular risk factors, such as hypercholesterolemia, hypertension and smoking alone do not account for the excess risk of cardiovascular morbidity and mortality in type-2 diabetes mellitus. Rather, the excess morbidity and mortality is linked to the disease itself. Type-1 diabetes is the major cause of long-term micro and macro vascular complications. Diabetic nephropathy is the single most common cause of kidney failure worldwide. Thus understanding the pathogenesis and preventing these long-term complications have been major goals of research in diabetes mellitus. The major focus of diabetes research is the prevention of diabetic complications by tight glycaemic control. It has been a well-established fact that high blood glucose is a major responsible component for micro vascular or macro vascular diabetic complications whether to a larger or lesser extent. In recent times it has been well established that amongst the various markers of glycaemic control, glycated haemoglobin (GHb) is the most reliable biomarker for long term diabetes management.

Diabetes Control and Complications Trial (DCCT) and the United Kingdom Perspective Diabetes Study (UKPDS) have shown the importance of tight glycaemic control in order to prevent or delay the micro vascular disease in diabetic patients. The Diabetes Control and Complications Trial (DCCT) demonstrated the association of HbA1c levels with the progression of diabetes complications. The risk of progression of diabetes complications increases exponentially with HbA1c (Glycated haemoglobin).

Glycated haemoglobin (GHb) is formed by a non-enzymatic, substrate-concentration dependent irreversible process of combination of aldehyde group of glucose and other hexoses with the amino-terminal valine of haemoglobin. The estimation of GHb has provided a dependable method of assessing glycaemic control in diabetic patients. Amongst the various markers of glycaemic control, glycated haemoglobin (GHb) has been established as the most reliable biomarker in monitoring of long-term progression of diabetic complications. According to WHO, HbA1c can be used as a diagnostic test for diabetes. An HbA1c of 6.5% is recommended as the cut point for diagnosing diabetes. Laboratory value for HbA1c test gives the glycated haemoglobin relative to total haemoglobin in the form of percentage value of glycated haemoglobin.

There are different methods available for glycated haemoglobin detection in laboratories as well as in point of care devices. Most of these methods are based upon the separation of glycated component from the total haemoglobin and then detection of total haemoglobin and glycated haemoglobin component by using two different techniques. After detection, the result can be calculated in the form of percentage glycated haemoglobin by dividing the glycated haemoglobin by total haemoglobin. In the present invention, we disclose the electrochemical method for the detection of percentage glycated haemoglobin (% GHb) using a single reagent technique.

Total haemoglobin is the biomarker for anaemia and other blood disorders. According to the WHO report, anaemia is a global health problem and affects 1.62 billion people worldwide. The highest prevalence of anaemia is in pre-school-age children, which is at 47.4%. One in four people are affected by anaemia and among them; pregnant women and preschool-age children are at the greatest risk.

Methaemoglobin is the oxidized form of haemoglobin in which the oxidation state of iron is +3. This form of haemoglobin cannot bind the oxygen. In healthy person, the percentage of methaemoglobin may vary in between 1-3%. This percentage may increase due to chemical exposures and oxidative stress. Methaemoglobin is a known biomarker for methaemoglobinaemia disorder.

Methaemoglobinemia is a disorder caused by oxidative stress and chemical exposure in which the iron center of heme prosthetic group oxidized and unable to bind the oxygen. The general treatment for methaemoglobinaemia is the methylene blue and ascorbic acid. Methaemoglobinemia can be treated using the organic dye methylene blue dye (MB).

However, methaemoglobin is a small percentage of the total haemoglobin, it is therefore necessary to provide an electrochemical method for the detection of total haemoglobin as well as methaemoglobin.

Myoglobin is monomeric hemeprotein, mainly found in muscle tissue, where it serves as intracellular oxygen storage site. Myoglobin in serum, is a well known marker for muscle tissue damage, and also myocardial infraction.

Most of known devices and methods that are used to detect haemoglobin are either based on immunological techniques or complex instrumentation like Raman spectroscopy and microfluidics, which are not best suitable for low cost point-of-care device.

It is therefore highly desirable to have a disposable device that can detect and quantify electrochemically, bioanalytes such as total haemoglobin, glycated albumin and methaemoglobin and myoglobin in blood samples.

U.S. Pat. No. 7,855,079B2 discloses a optical method for glycated haemoglobin using the enzymatic techniques.

US2008206563B2 discloses a method of determining the percentage of glycated hemoglobin in a blood sample, wherein at least one of the assay steps is performed electrochemically. The method includes determining the total amount of hemoglobin in a sample by electrochemically measuring, in an oxygen electro-reduction reaction at a cathode, the amount of oxygen in the sample.

U.S. Pat. No. 8,460,525B2 discloses an electrochemical device for determining the percentage of glycated hemoglobin in a blood sample. The device includes a cathode and anode and one or more cells. The device may include an enzyme capable of reducing oxygen to water for determining the total amount of haemoglobin in a sample by electrochemically measuring, in an oxygen electro-reduction reaction at a cathode, the amount of oxygen in the sample.

U.S. Pat. No. 8,557,590 B2 discloses a method for measuring glycated haemoglobin includes haemolyzing a blood sample with a haemolysate; reacting the haemolyzed blood sample with bead conjugates in which beads are conjugated with glycated haemoglobin binding materials; measuring the amount of total haemoglobin in there acted blood sample; isolating normal haemoglobin from the glycated haemoglobin conjugated with the bead conjugates.

US2012/0261257A1 discloses the electrochemical detection of total haemoglobin and glycated haemoglobin by using the two different techniques. Glycated haemoglobin is detected using the graphene-modified electrode.

WO2013096856A1 discloses the detection of glycated haemoglobin based on Raman spectroscopy.

EP0256851B1 discloses an electrochemical method for haemoglobin detection based on ferricyanide mediator.

EP2568281A1 discloses the electrochemical detection of haemoglobin based on the oxidation of haemoglobin.

U.S. Pat. No. 4,876,205 discloses an electrochemical assay for haemoglobin by monitoring the current changes produced on reduction of ferricyanide to ferrocyanide by haemoglobin.

US20040186359A1 discloses an optical biosensor for myoglobin detection based on affinity legends or binding members that bind specifically to a marker being monitored.

J. Clin. Chim. Acta, 30 (1970) 679-682 by Hegesh et al., discloses a detection of methaemoglobin based on cyanide reaction with methaemoglobin and the change in light absorption at 632 nm is measured.

OBJECTS OF THE PRESENT INVENTION

The primary object of the present invention is to provide an electrochemically active device for collecting and retaining a blood sample having non-electrochemically active haemoglobin bioanalytes and its complexes, for a subsequent quantitative measurement of haemoglobin (Hb), glycated haemoglobin (GHb), methaemoglobin (MetHb) and myoglobin, in reduced volumes of blood samples.

An object of the present invention to provide a device holder that is adapted to receive an electrochemically active device for a subsequent quantitative measurement of haemoglobin (Hb), glycated haemoglobin (GHb), methaemoglobin (MetHb) and myoglobin, in reduced volumes of blood samples.

Another object of the present invention is to provide a point-of-care biosensor, adapted to receive an electrochemically active device for the detection and quantitative measurement of haemoglobin (Hb), glycated haemoglobin (GHb), methaemoglobin (MetHb) and myoglobin, in reduced volumes of blood samples, through a measurement of redox current flowing through the electrochemically active device, on the application of an redox potential.

It is also an object of the present invention to provide a method for the detection and quantitative measurement of haemoglobin (Hb), glycated haemoglobin (GHb), methaemoglobin (MetHb) and myoglobin, in reduced volumes of blood samples, through an accurate measurement redox current flowing through the electrochemically-active electrodes.

It is also an object of the present invention to provide a method for the quantitative measurement of glycated haemoglobin, in reduced volumes of blood sample.

BRIEF DESCRIPTION OF THE DRAWINGS

FIG. 7(a) is schematic top view of the electrochemically active device of the present invention with two sets of a three-electrode arrangement to measure percentage methaemoglobin in blood sample.

FIG. 7(b) is a schematic cross-sectional view of the electrochemically active device of the present invention, where receptor-membrane is arranged on the electrodes along with receptor-membrane and lysing-membrane with lysing salt layer.

FIG. 7(c) is a schematic cross-sectional view of the electrochemically active device of the present invention, where receptor layer and lysing salt layer are arranged on the receptor-membrane.

FIG. 7(d) is a schematic cross-sectional view of the electrochemically active device of the present invention, where receptor layer is arranged on the electrodes along with lysing-membrane and lysing salt layer.

FIG. 7(e) is a schematic cross-sectional view of the electrochemically active device of the present invention, where receptor layer and lysing salt layer are arranged on the electrodes layer.

SUMMARY OF THE PRESENT INVENTION

Figure 1:
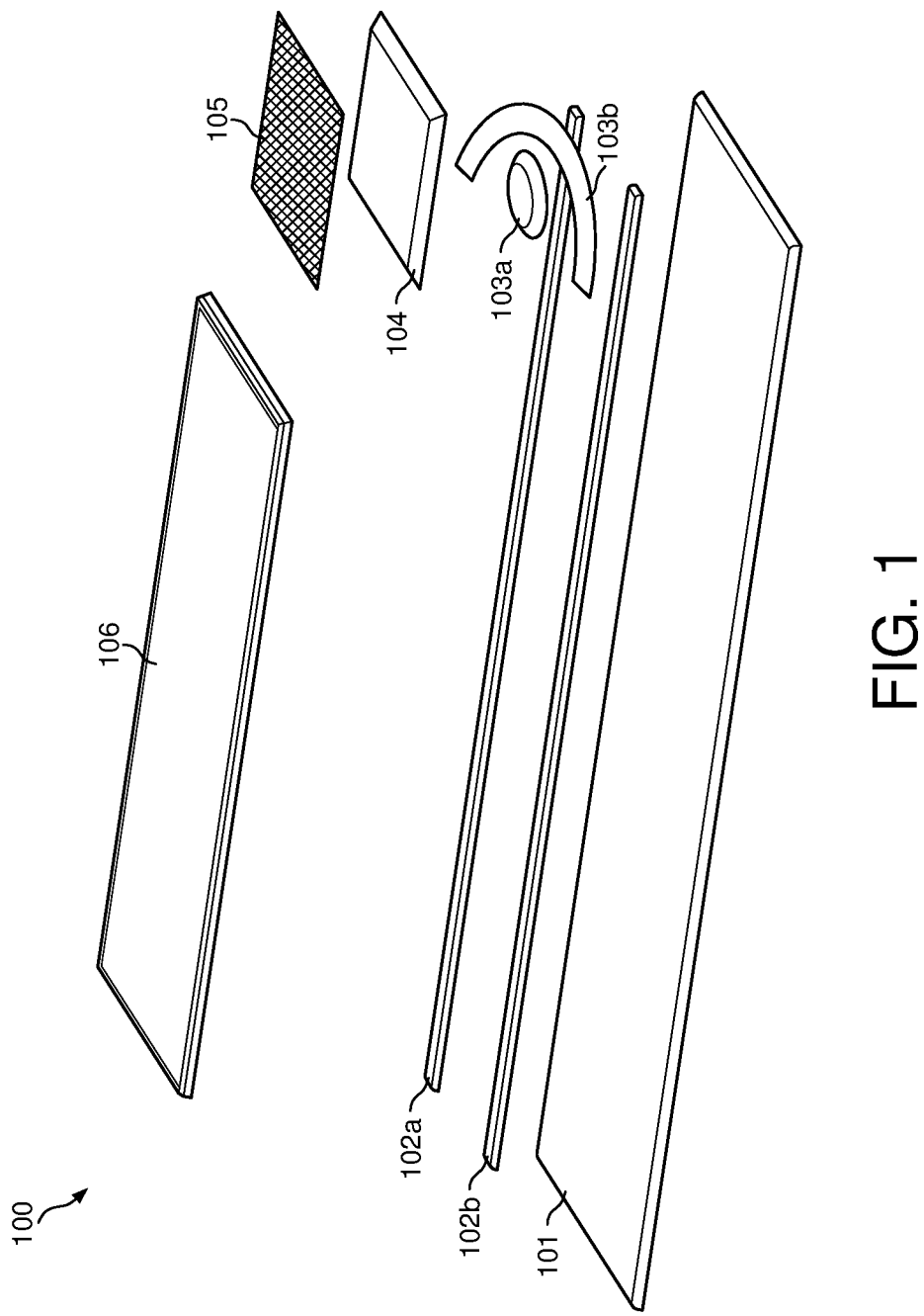
FIG. 1 is a schematic exploded view of the electrochemically active device, depicting a two-electrode arrangement, for receiving and converting non-electrochemically active heamoglobin bioanalyte and its complexes in reduced volume of blood samples, into electrochemically active bioanalyte and complexes.

The present invention provides an electrochemically active device for collecting and retaining a blood sample with at least a two-electrode member connected to conductive tracks. A receptor with an integral receptor-membrane arranged on the two-electrode member, to receive non-electrochemically active heamoglobin bioanalyte and its complexes from red blood cells (RBC) of said blood sample, through a lysing agent and convert the non-electrochemically active heamoglobin bioanalyte and its complexes, into an electrochemically active bioanalyte and its electrochemically active complexes. The present invention also provides a point-of-care biosensor incorporated with the device of the present invention and method of measuring for the detection and quantitative measurement of concentrations of haemoglobin (Hb), glycated haemoglobin (GHb), methaemoglobin (MetHb) and myoglobin, in reduced volumes of blood samples. The device, point-of-care biosensor and the method of the present invention facilitate accurate measurements concentrations of haemoglobin (Hb), glycated haemoglobin (GHb), methaemoglobin (MetHb) and myoglobin by determining redox current values in the reduced volumes of blood samples.

DETAILED DESCRIPTION OF THE INVENTION

Accordingly, the present invention provides an electrochemically active device for collecting and retaining a blood sample. The present invention also provides a holder for holding the electrochemically active device with the blood sample and a point-of-care biosensor for an accurate detection and quantitative measurement of haemoglobin (Hb), glycated haemoglobin (GHb), methaemoglobin (MetHb) and myoglobin bioanalytes, by measuring redox current values, in the reduced volumes of blood samples, having these bioanalytes.

In an aspect of the present invention the electrochemically active device for collecting and retaining a blood sample, is provided with at least a pair of electrically conductive tracks arranged on a substrate. An electrode member, with at least a pair of electrodes is connected to the conductive tracks and the electrode member is functionalized with a receptor, to convert the desired haemoglobin bioanalyte and its complexes into electrochemically active bioanalytes. Thus the receptor, which is in chemical contact with a lysing agent, is arranged to receive the non-electrochemically active bioanalytes from the blood sample, of reduced volume and convert the same into electrochemically active bioanalytes for the measurement of their concentrations.

In another aspect of the present invention a holder for holding the electrochemically active device of the present invention, is provided with a housing having a device detection, data storage and signal conditioning circuitry. A Universal Serial Bus (USB) connector is arranged at one end of the housing and an electrically conductive port is arranged at the other end of the housing. The holder is adapted to receive the electrochemically active device through the electrically conductive port.

In yet another aspect of the present invention, a point-of-care biosensor for measuring a concentration of a haemoglobin bioanalyte and its complexes in a blood sample is provided. The point-of-care biosensor comprises a housing with a display member and an interface, for inserting the electrochemically active device of the present invention. The point-of-care biosensor is provided with slots for inserting micro USB and a micro SD card. A digital controller is arranged in the housing and configured to apply a redox potential to the device, which is loaded with the blood sample having a haemoglobin bioanalyte and its complexes. The digital controller is also configured to display concentration of the haemoglobin bioanalyte and its complexes by measuring a corresponding redox current and linearly matching it to the concentrations of haemoglobin and its complexes.

In further aspect of the present invention a method for measuring a concentration of a bioanalyte in a reduced volume of a blood sample by applying a redox potential to at least a two-electrode member functionalized with a receptor, which makes the non-electrochemically active haemoglobin bioanalyte and its complexes electrochemically active. The receptor is loaded with a reduced volume of desired blood sample having a haemoglobin bioanalyte and its complexes and determining concentrations of the haemoglobin bioanalyte in the blood sample, by linearly matching with a corresponding redox current.

In yet another aspect of the present invention, non-electrochemically active bioanalyte is haemoglobin (Hb), glycated haemoglobin (GHb), methaemoglobin (MetHb) and myoglobin.

Now, the preferred embodiments of the invention are described by referring to the accompanied drawings. FIG. 1 depicts an electrochemically active device adapted to collect and retain a biological sample, for subsequent measurement of haemoglobin analyte present in the biological sample.

The device 100 as shown in FIG. 1 is provided with a substrate 101, which acts as base on which other constituents of the device are constructed. The substrate 101, in this embodiment is exemplarily shown as an elongated circular structure. However, it is understood here that the substrate 101 can take other shapes such as rectangular, or circular, depending on the shape and configuration of a biosensor that holds the device 100. The substrate 101 can be made of any suitable rigid or flexible material that is suitable for the incorporation of patterned electrodes. For instance, materials such as polyvinylchloride (PVC), polyethylene terephthalate (PET), polymethylmethacrylate (PMMA), epoxy fiber composites, polyamides composites, and paper can be used as preferred materials for the substrate 101. Whereas, the preferred rigid materials for the substrate 101 can be ceramic, glass or any other like materials. In any case, the selection of suitable material for the substrate 101 is made to ensure that the substrate 101 can not only provide a desirable strength and flexibility but also can act as an electrical insulator. Advantageously the substrate 101 is hydrophilic in nature to prevent percolation of the biological sample, when it comes in physical contact with the substrate 101. The surface of the substrate 101 is generally provided with a smooth texture. However, the substrate 101 can also be provided with a rough surface and/or with cavities or wells. The edges of the substrate 101 are also provided with suitable profiles, such as tapered or curved, to facilitate an easy ingress into and egress out of the biosensor.

A pair of conductive tracks 102a and 102b are arranged on the substrate 101. The conductive tracks 102a and 102b are formed by using any patterning method such as screen printing, lithography, thermal evaporation, sputtering, laser patterning, preferably screen-printing. In an exemplary aspect, in FIG. 1, pair of conductive tracks 102a and 102b are formed for implementation. However, the required number of conductive tracks can be suitably increased or varied. The routing of the conductive tracks 102a and 102b are exemplarily shown as straight tracks in FIG. 1. Other suitable configurations for the conducting tracks such as polygons can be used. The material for the conductive tracks 102a and 102b can be an electrically conductive materials such as copper, aluminum, gold, silver, platinum, carbon, or any other suitable electrically conducting material or alloys of these materials. The material for the conducting tracks 102a and 102b can also be electrochemically active such as gold, platinum, mercury, carbon, glassy carbon and graphite. The conducting tracks 102a and 102b are used to establish an electrical connection with the biosensor of the present invention as hereinafter described.

Pair of electrodes 103a and 103b are electrically connected to the conducting tracks 102a and 102b respectively, as shown in FIG. 1. The electrodes 103a and 103b are overlaid on the conducting tracks 102a and 102b and arranged at the terminal ends of the conducting tracks 102a and 102b, so as to form a layer above the conducting tracks 102a and 102b, as shown in FIG. 1. The material for the electrodes 103a and 103b are selected from metals, organics or alloys, which are electrochemically active, such as gold, platinum, mercury, carbon, glassy carbon and graphite. In the arrangement of electrodes as shown in FIG. 1, the electrode 103a acts as a working electrode and whereas the electrode 103b is a counter electrode.

A receptor-membrane 104 is arranged on the pair of electrodes 103a and 103b as shown in FIG. 1, which acts as a base member for the integration of a receptor as hereinafter described. The material for the membrane 104 can be polymer, cellulose, nitrocellulose, nylon, cotton fabric, filter paper, or any other commercially available membrane such as BIODYNE membrane from PAL lifesciences or GE Healthcare membrane etc.

The device 100 of present invention is used for the detection and quantitative measurement of bioanalytes such as haemoglobin (Hb), glycated haemoglobin (GHb), methaemoglobin (MetHb) and myoglobin, either individually or in combination, in human blood samples.

Accordingly, in the present invention a receptor 105, which converts the non-electrochemically active haemoglobin bioanalyte and its complexes into corresponding electrochemically active bioanalytes, is arranged on the electrodes 103a and 103b, along with a receptor-membrane 104. The receptor-membrane 104 is primarily adapted to hold the receptor 105 or to provide a base to hold substances, as hereinafter described, which act as the receptor 104. The receptor-membrane 104 as used is with desired porosity, which is larger than the size of the haemoglobin bioanalyte, which is preferably in the range of 7 nm to 14 microns, to facilitate the desired levels of permeability of the bioanalytes. The receptor-membrane 104 can also be made an integral part of the receptor 105. The material for the receptor-membrane 104 is a polymer, cellulose, fabric, a paper or any other suitable materials.

The receptor 105, in this preferred embodiment, is shown as a layer of electrochemically active substance, such as an organic, an inorganic substance or a substance, which is a combination of these substances.

Accordingly the organic substance for the receptor 105 is selected from heterocyclic organic substances having an N-heteroatom, such as pyridine, pyridine HCl, hydroxypyridine, cyanopyridine, imidazole, pyrazole, indole, pyramidine and purine. In the present invention pyridine and imidazole are selected as preferred organic substances for the receptor 105.

Whereas, the suitable inorganic substance for the receptor 105 is an alkali, preferably NaOH and KOH.

In an aspect where a combination of organic and inorganic substances are used for the receptor 105, the preferred organic substances is methylene blue (MB) along with inorganic oxidizing agents, such as sodium nitrate ($NaNO_3$), sodium nitrite ($NaNO_2$) or sodium dodecyl sulphate.

In yet another aspect of the present invention, the receptor-membrane 104 that is adopted for use, to measure the concentration levels of glycated haemoglobin (GHb) in a blood sample is treated with a boronate affinity agent. The boronate agent is selected suitable boronic acids and derivatives such as phenyl boronic acid (PBA), aminophenyl boronic acid (APBA) and derivatives thereof, preferably aminophenyl boronic acid (APBA).

In an alternate aspect of the present invention, the receptor 105 can also be directly disposed on the electrode surface, in the absence of the receptor-membrane 104, for detecting the bioanalyte.

A lysing agent is arranged to be in chemical contact with the receptor 105 and preferably arranged on a lysing membrane, to receive the blood sample and release non-electrochemically active heamoglobin bioanalyte and its complexes from red blood cells (RBC) of said blood sample, so that the receptor 105 can make the bioanalyte as electrochemically active The lysing agent is selected from the group consisting of diocetyl sodium sulfosuccinate, sodium dodecyl benzene sulphonate, lauryl dimethylamine oxide, octyl phenoxy poly ethoxy ethanol, potassium ferricyanide, sodium lauryl sulfate, lithium dodecyl sulfate, sodium nitrite, cetyle trymethyl ammonium bromide, sodium dodecyl sulfate, sodium deoxychelate, N-lauroylsarcosine, didodecyldimethylammonium bromide, octylphenol ethylene oxide condensate and hydrochloric acid, preferably sodium dodecyl sulfate and didodecyldimethylammonium bromide.

The bioanalytes, that are used in the present invention, for their quantitative measurement of their concentrations, include haemoglobin (Hb), glycated haemoglobin (GHb), methaemoglobin (MetHb) and myoglobin, in their non-electro chemically active forms.

The initiation of chemical contact of the receptor 105 with the electrodes 103a and 103b is performed in the following manner. A solution of receptor 105 is prepared and dispensed on the electrodes 103a and 103b with the 104 and dried to form a solid chemical layer on the electrodes 103a and 103b and the membrane 104.

Alternately, the receptor solution is pre-mixed with the desired lysed blood sample and a reduced volume of the pre-mixed solution is dispensed on the electrodes 103b and 103b with the membrane 104.

In yet another aspect of the present invention, the receptor solution is prepared separately and dispensed on the electrodes 103a and 103b having the membrane 104. Thereafter, the desired blood sample having haemoglobin bioanalyte is applied on the electrodes.

A passivation layer 106 is arranged to cover the conducting tracks as shown in FIG. 1. The passivation layer 106 is used to provide protection for the conductive elements of the device and to precisely define the electrode region.

Figure 2:
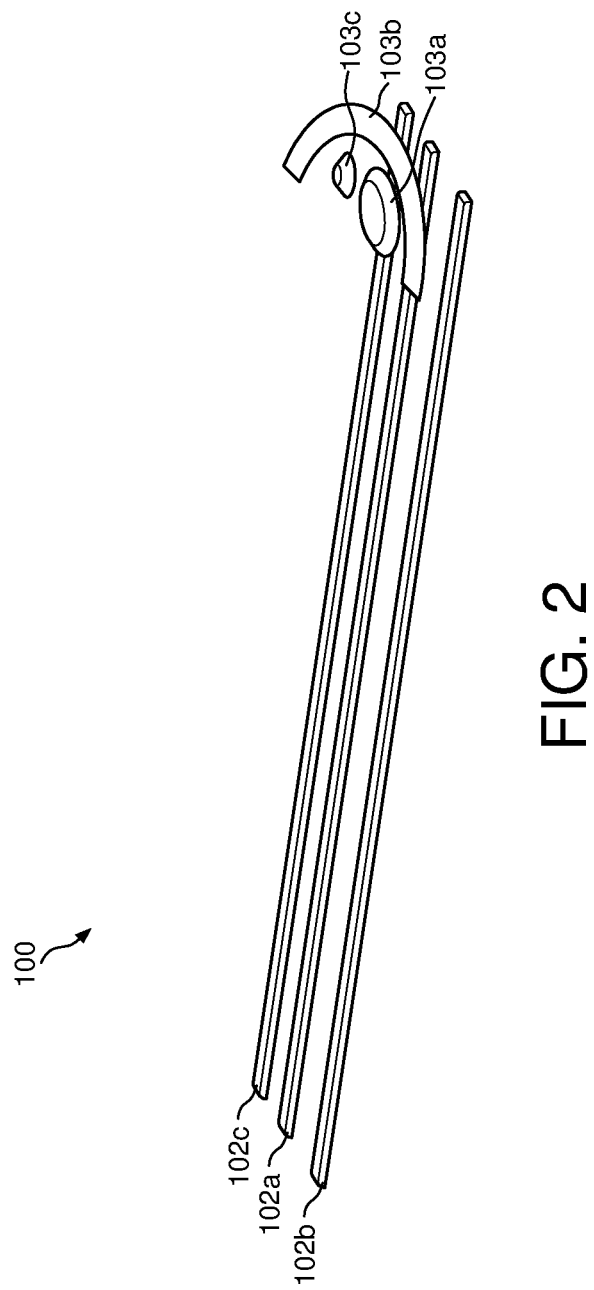
FIG. 2 is a schematic exploded view of a three-electrode arrangement of the electrochemically active device, in accordance with an aspect of the present invention.
Figure 3A:
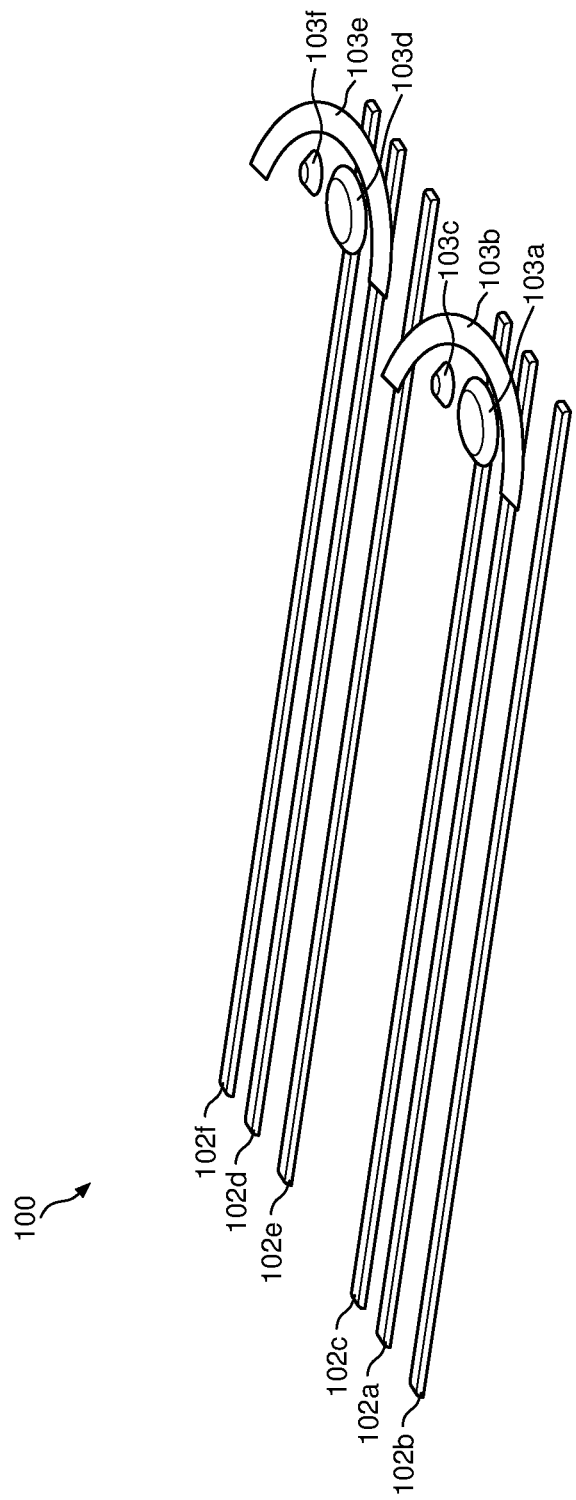
FIG. 3(a) is a schematic exploded view of two pairs of three-electrode arrangement, of the electrochemically active device, in accordance with yet another aspect of the present invention.
Figure 3B:
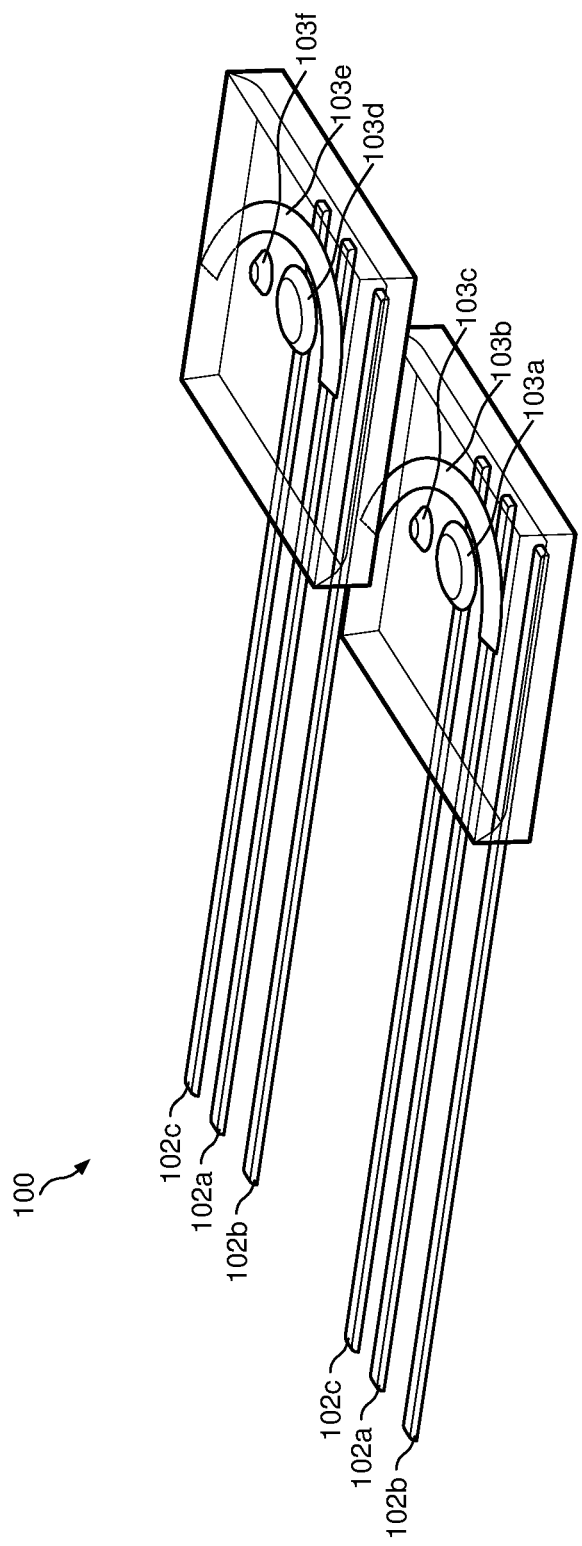
FIG. 3(b) is a schematic exploded view of two pairs of three-electrode arrangement with trays, of the electrochemically active device, in accordance with yet another aspect of the present invention.

In yet another aspect of the present invention, as shown in FIG. 2, an arrangement of set of three electrodes 103a, 103b and 103c is implemented in conjunction with a receptor as shown in FIG. 1, where the electrodes 103a, 103b and 103c are connected to the conducting tracks 102a, 102b and 102c respectively, to collect and retain a biological sample. The increased number of electrodes facilitates the detection of a single bio-analyte in the blood sample with an increased accuracy. In this implementation, the electrode 103c acts as a reference electrode. The preferred material for the reference electrode 103c is silver (Ag), a silver chloride (AgCl), silver/silver chloride (Ag/AgCl) or saturated calomel, where the potential of the electrodes does not change with time. In yet another aspect of the present invention as shown in FIG. 3 (a), two pairs of three-electrodes 103a, 103b, 103c, 103d, 103e and 103f are arranged on the conducting tracks 102a, 102b, 102c, 102d, 102e and 102f and are adapted for use to measure the concentration of multiple bio-analytes, in given blood samples. In this aspect, shielded wells or trays are arranged on the electrodes to demarcate different sensing areas, as illustrated in FIG. 3(b), to facilitate an independent sensing of the blood samples. Accordingly, two separate receptors are provided in conjunction with each of the pair of the electrodes to receive these samples and separate measurement of concentrations of haemoglobin and its complexes in these two different blood samples is performed. In addition, if deemed necessary, physical partitions may be provided to separate the electrodes.

Figure 4A:
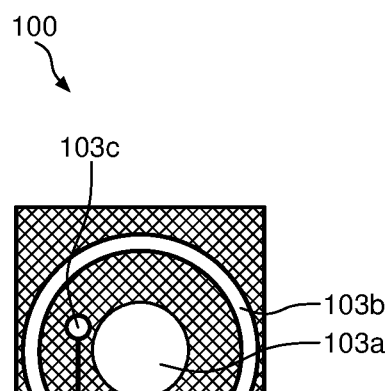
FIG. 4 (a) is a schematic top view of the electrochemically active device with a three-electrode arrangement for measuring haemoglobin.
FIG. 4(b) is a schematic cross-sectional view of the electrochemically active device, where the receptor layer is arranged on the surface of the receptor-membrane, and lysing agent is arranged on lysing membrane.
FIG. 4(c) is a schematic cross-sectional view of the electrochemically active device, where the receptor and the lysing salt layer are arranged on the receptor-membrane, on the surface of the electrodes.
FIG. 4(d) is a schematic cross-sectional view of the electrochemically device, where the receptor is arranged on the surface of the electrode and lysing-membrane with a lysing salt layer, is arranged on the surface of the receptor.
FIG. 4(e) is a schematic cross-sectional view of the electrochemically device, where the receptor and lysing agent are applied on the electrodes.
FIG. 4(f) is a schematic cross-sectional view of the electrochemically device, where the receptor and lysing agent are integral part of the electrodes.

As shown in FIG. 4(a), depicts a top view of the electrochemically active device for the detection of haemoglobin in blood sample.

Figure 4B:
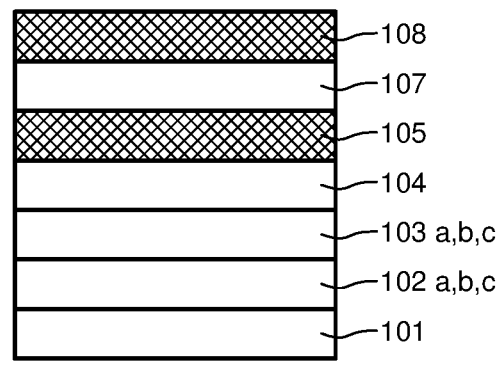

FIG. 4(b), which is a corresponding cross-sectional view depicting a substrate 101 on the surface of which conducting tracks 102a, 102b, 102c are arranged. A 3-electrode arrangement with a working electrode 103a, counter electrode 103b and reference electrode 103c connected to the conducting tracks 102a, 102b, 102c. The receptor-membrane 104 is arranged on surface of the electrodes 103a, 103b and 103c. The receptor layer 105 is arranged on the surface of the receptor-membrane 104. The lysing-membrane 107 is arranged on the surface of the receptor layer 105. The lysing salt layer 108 is arranged on the surface of the lysing-membrane 107.

Figure 4C:
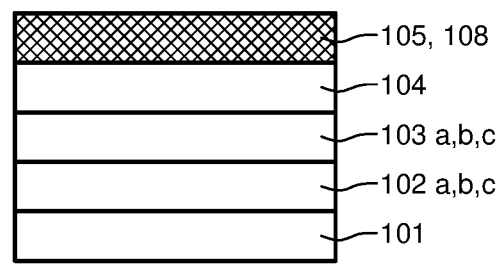

FIG. 4(c), which is a corresponding cross-sectional view depicting a substrate 101 on the surface of which conducting tracks 102a, 102b, 102c are arranged. A 3-electrode arrangement with a working electrode 103a, counter electrode 103b and reference electrode 103c connected to the conducting tracks 102a, 102b, 102c. The receptor layer 105 and lysing salt layer 108 both are arranged on the receptor-membrane 104.

Figure 4D:
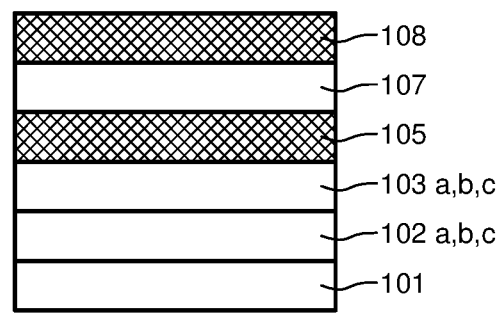

FIG. 4(d), which is a corresponding cross-sectional view depicting a substrate 101 on the surface of which conducting tracks 102a, 102b, 102c are arranged. A 3-electrode arrangement with a working electrode 103a, counter electrode 103b and reference electrode 103c connected to the conducting tracks 102a, 102b, 102c. The receptor layer 105 is arranged on surface of the electrodes 103a, 103b and 103c. The lysing-membrane 107 is arranged on the surface of the receptor layer 105. The lysing salt layer 108 is arranged on the surface of the lysing-membrane 107.

Figure 4E:
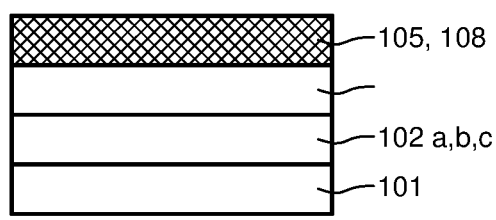

FIG. 4(e), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor layer 105 and lysing salt layer 108 both are arranged on the top of the electrodes layer 103a, 103b and 103 c.

Figure 4F:
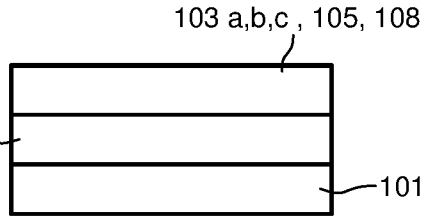

FIG. 4(f), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor layer 105 and lysing salt layer 108 both are the integral part of the electrodes layer 103a, 103b and 103c.

The embodiments as shown in FIG. 4(a),(b),(c),(d),(e) and (f) are used to measure haemoglobin bioanalyte in blood samples.

Figure 5A:
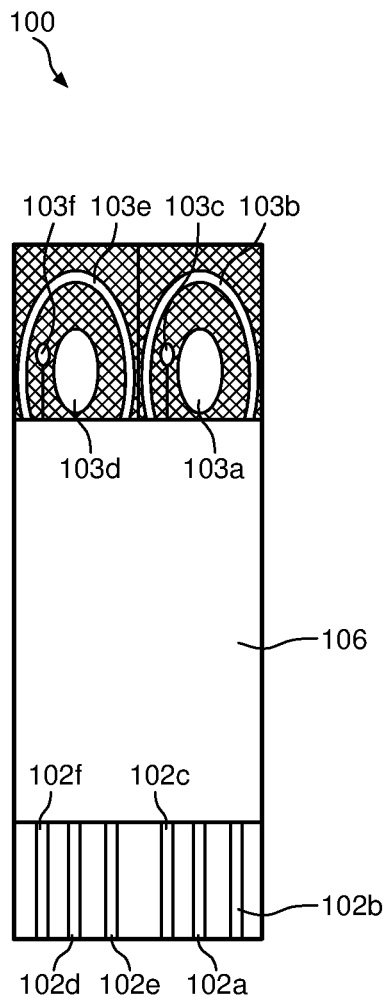
FIG. 5(a) is schematic top view of the electrochemically active device of the present invention with two sets of three-electrode arrangement, for the measurement of percentage glycated haemoglobin.

As shown in FIG. 5(a), illustrates a top view of the electrochemically active device of the present invention for the detection of glycated haemoglobin.

Figure 5B:
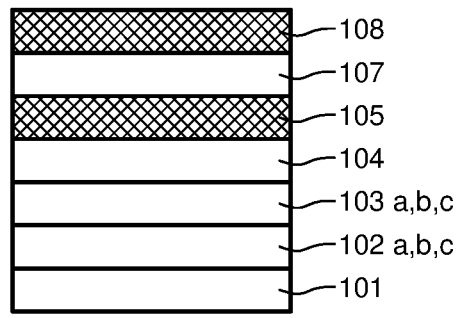
FIG. 5(b) is a schematic cross-sectional view of the electrochemically active device, where the receptor is arranged on the surface of the receptor-membrane and the lysing-membrane with lysing salt layer is arranged on the surface of the receptor layer.

FIG. 5(b), which is a corresponding cross-sectional view depicting a substrate 101 on the surface of which conducting tracks 102a, 102b and 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor-membrane 104 is arranged on surface of the electrodes 103a, 103b and 103c. The receptor layer 105 is arranged on the surface of the receptor-membrane 104. The lysing-membrane 107 is arranged on the surface of the receptor layer 105. The lysing salt layer 108 is arranged on the surface of the lysing-membrane 107.

Figure 5C:
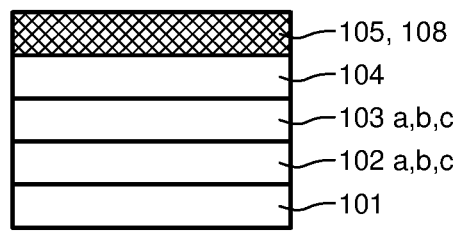
FIG. 5(c) is a schematic cross-sectional view of the electrochemically active device of the present invention, where the receptor and the lysing salt layer are arranged on the receptor-membrane.
Figure 5D:
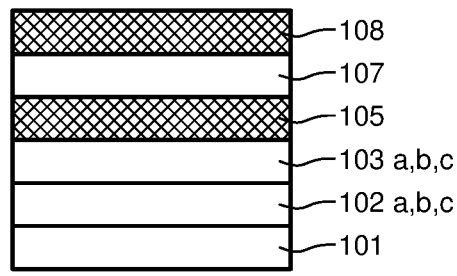
FIG. 5(d) is a schematic cross-sectional view of the electrochemically active device of the present invention, where the receptor is arranged on the surface of the electrode and lysing-membrane with a lysing salt layer, is arranged on the surface of the receptor.

FIG. 5(c), which is a corresponding cross-sectional view depicting a substrate 101 on the surface of which conducting tracks 102a, 102b and 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor layer 105 and lysing salt layer 108 both are arranged on the receptor-membrane 104.

FIG. 5 (d), which is a corresponding cross-sectional view depicting a substrate 101 on the surface of which conducting tracks 102a, 102b and 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor layer 105 is arranged on surface of the electrodes 103a, 103b and 103c. The lysing-membrane 107 is arranged on the surface of the receptor layer 105. The lysing salt layer 108 is arranged on the surface of the lysing-membrane 107.

Figure 5E:
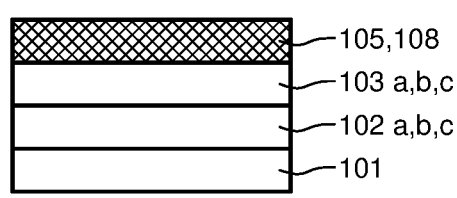
FIG. 5(e) is a schematic cross-sectional view of the electrochemically active device, where the receptor and lysing salt layer are arranged on the electrodes.

FIG. 5(e), which is a corresponding cross-sectional view depicting a substrate 101 on the surface of which conducting tracks 102a, 102b, 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor layer 105 and lysing salt layer 108 both are arranged on the top of the electrodes layer 103a, 103b and 103 c.

Figure 5F:
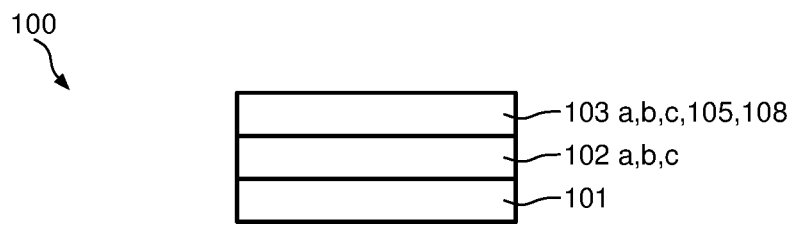
FIG. 5(f) is a schematic cross-sectional view of the electrochemically active device of the present invention, where the receptor and lysing salt layer are integrally arranged with the electrodes.

FIG. 5(f), which is a corresponding cross-sectional view depicting a substrate 101 on the surface of which conducting tracks 102a, 102b and 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor layer 105 and lysing salt layer 108 both are the integral part of the electrodes layer 103a, 103b and 103 c.

Figure 5G:
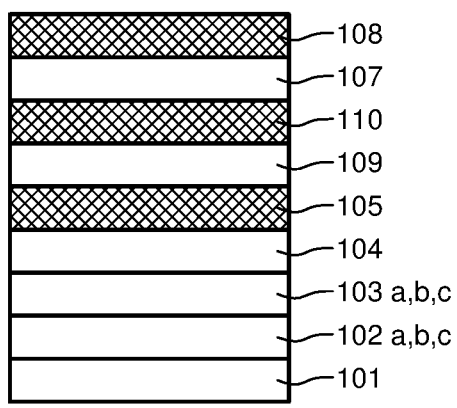
FIG. 5(g) is a schematic cross-sectional view of the electrochemically active device, where receptor with receptor-membrane are arranged on electrodes, glycated haemoglobin filtration membrane and boronate affinity agent arranged on receptor layer and a lysing-membrane with lysing salt at the top.

FIG. 5(g), which is a corresponding cross-sectional view depicting a substrate 101 on the surface of which conducting tracks 102a, 102b and 102c are arranged in the right half portion of the substrate 101. A 3-electrode arrangement in the right half portion of the substrate 101 with a working electrode 103a, counter electrode 103b and reference electrode 103c connected to the conducting tracks 102a, 102b and 102c. The receptor-membrane 104 is arranged on surface of the electrodes 103a, 103b and 103c. The receptor layer 105 is arranged on the surface of the receptor-membrane 104. A glycated haemoglobin filtration membrane 109 is arranged on top of the receptor layer 105. The boronic acids based boronate affinity substances 110 is arranged on top of the haemoglobin filtration membrane 109. The lysing-membrane 107 is arranged on the surface of the boronate affinity agent 110. The lysing salt layer 108 is arranged on the surface of the lysing-membrane 107.

Figure 5H:
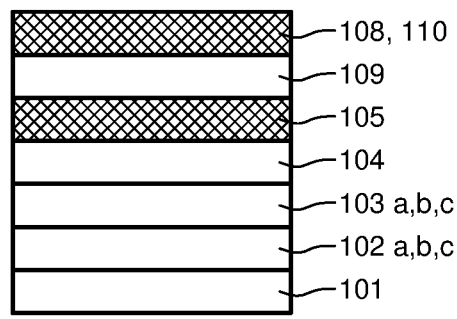
FIG. 5(h) is a schematic cross-sectional view of the electrochemically active device of the present invention, where the receptor is arranged on receptor membrane on top of electrodes, glycated haemoglobin filtration membrane arranged on top of receptor, and lysing salt and boronate affinity agent together arranged on top of glycated haemoglobin filtration membrane.
Figure 5I:
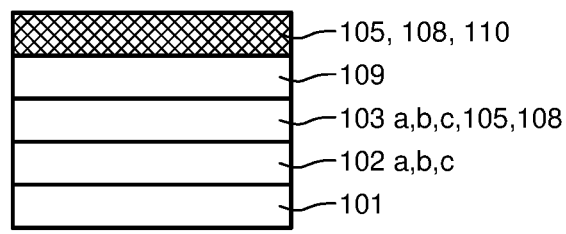
FIG. 5(i) is a schematic cross-sectional view of the electrochemically active device of the present invention, where the receptor, lysing salt layer and boronate affinity agent are together arranged on glycated haemoglobin filtration membrane sitting on top of electrodes.

FIG. 5(h), which is a corresponding cross-sectional view depicting a substrate 101 on the surface of which conducting tracks 102a, 102b and 102c are arranged in the right half portion of the substrate 101. A 3-electrode arrangement in the right half portion of the substrate 101 with a working electrode 103a, counter electrode 103b and reference electrode 103c connected to the conducting tracks 102a, 102b, 102c. The receptor layer 105 is arranged on the receptor-membrane 104. A glycated haemoglobin filtration membrane 109 is arranged on top of the receptor layer 105. The boronic acids based boronate affinity substances 110 along with the lysing salt layer 108 are arranged on top of the haemoglobin filtration membrane 109.

FIG. 5 (i), which is a corresponding cross-sectional view depicting a substrate 101 on the surface of which conducting tracks 102a, 102b and 102c are arranged in the right half portion of the substrate 101. A 3-electrode arrangement in the right half portion of the substrate 101 with a working electrode 103a, counter electrode 103b and reference electrode 103c connected to the conducting tracks 102a, 102b and 102c. The receptor layer 105 the lysing salt layer 108 and the boronate affinity substances 110 are together arranged on a glycated haemoglobin filtration membrane 109 sitting on top of electrodes.

The embodiments as shown in FIG. 5 (a) (b),(c),(d),(e), (f),(g),(h) and (i) are used to measure the percentage glycated haemoglobin (% GHb) bioanalyte in blood samples.

Figure 6A:
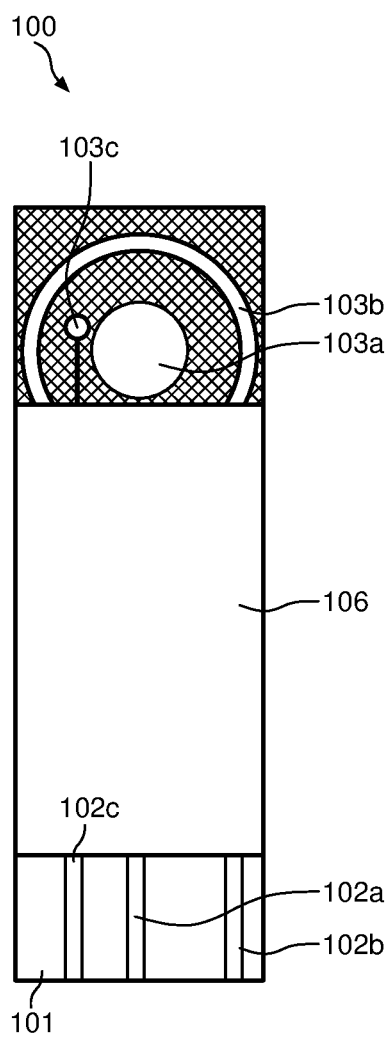
FIG. 6(a) is schematic top view of the electrochemically active device of the present invention with two sets of a three-electrode arrangement for quantitative measurement of absolute methaemoglobin.

As shown in FIG. 6(a), illustrates a top view of the electrochemically active device of the present invention, for the detection of absolute methaemoglobin bioanalyte in blood sample.

Figure 6B:
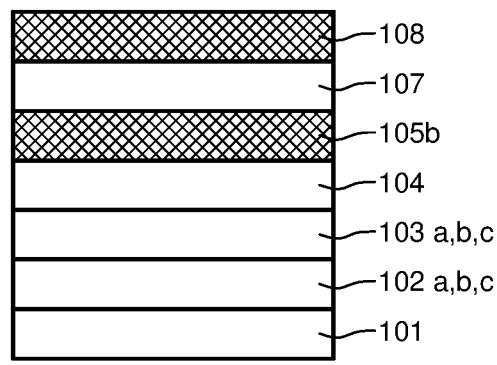
FIG. 6(b) is a schematic cross-sectional view of the electrochemically active device of the present invention, where receptor-membrane with receptor layer and lysing membrane with lysing salt layer are arranged on the electrodes.

FIG. 6(b), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor-membrane 104 is arranged on surface of the electrodes 103a, 103b and 103c. The receptor layer 105b is arranged on the surface of the receptor-membrane 104. The lysing-membrane 107 is arranged on the surface of the receptor layer 105b. The lysing salt layer 108 is arranged on the surface of the lysing-membrane 107.

Figure 6C:
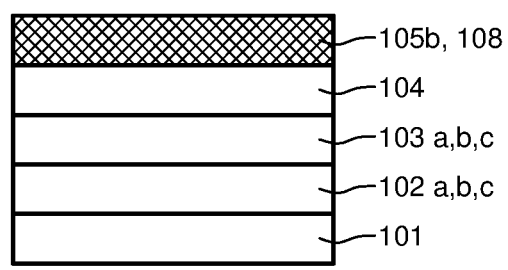
FIG. 6(c) is a schematic cross-sectional view of the electrochemically active device of the present invention, where receptor layer and lysing salt layer are arranged on receptor-membrane.

FIG. 6(c), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor layer 105 and lysing salt layer 108 both are arranged on the receptor-membrane 104.

Figure 6D:
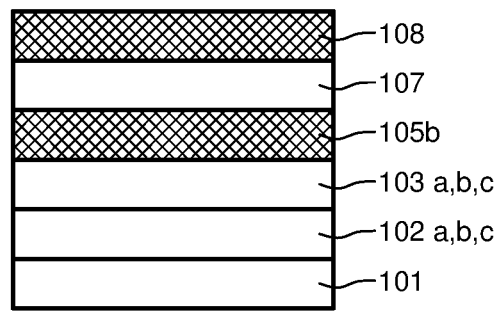
FIG. 6(d) is a schematic cross-sectional view of the electrochemically active device of the present invention, where the receptor layer is arranged on the electrodes with a lysing-membrane and lysing salt.

FIG. 6(d), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor layer 105 is arranged on surface of the electrodes 103a, 103b and 103c. The lysing-membrane 107 is arranged on the surface of the receptor layer 105. The lysing salt layer 108 is arranged on the surface of the lysing-membrane 107.

Figure 6E:
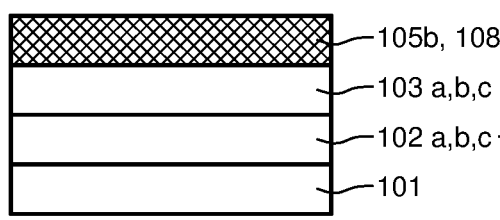
FIG. 6(e) is a schematic cross-sectional view of the electrochemically active device of the present invention, where receptor layer and lysing salt layer are arranged on top of the electrodes layer.

FIG. 6(e), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor layer 105 and lysing salt layer 108 both are arranged on the top of the electrodes layer 103a, 103b and 103c.

Figure 6F:
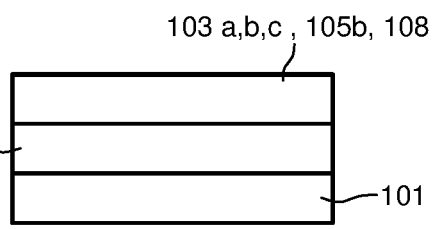
FIG. 6(f) is a schematic cross-sectional view of the electrochemically active device of the present invention, where receptor layer and lysing salt layer are the integral part of the electrodes layer.

FIG. 6(f), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor layer 105 and lysing salt layer 108 both are the integral part of the electrodes layer 103a, 103b and 103c.

The embodiments as shown in FIG. 6(a)(b),(c),(d),(e) and (f) are used to measure absolute methaemoglobin (MetHb) bioanalyte in blood samples.

As shown in FIG. 7(a), illustrates a top view of the electrochemically active device of the present invention for percentage methaemoglobin measurement in blood sample.

FIG. 7(b), which is a corresponding cross-sectional view depicting a substrate 101 on the surface of which conducting tracks 102a, 102b and 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor-membrane 104 is arranged on surface of the electrodes 103a, 103b and 103c. The receptor layer 105a is arranged on the surface of the receptor-membrane 104. The lysing-membrane 107 is arranged on the surface of the receptor layer 105a. The lysing salt layer 108 is arranged on the surface of the lysing-membrane 107.

FIG. 7(c), which is a corresponding cross-sectional view depicting a substrate 101 on the surface of which conducting tracks 102a, 102b, 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor layer 105a and lysing salt layer 108 both are arranged on the receptor-membrane 104.

FIG. 7(d), which is a corresponding cross-sectional view depicting a substrate 101 on the surface of which conducting tracks 102a, 102b and 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor layer 105a is arranged on surface of the electrodes 103a, 103b and 103c. The lysing-membrane 107 is arranged on the surface of the receptor layer 105a. The lysing salt layer 108 is arranged on the surface of the lysing-membrane 107.

FIG. 7(e), which is a corresponding cross-sectional view depicting a substrate 101 on the surface of which conducting tracks 102a, 102b and 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor layer 105a and lysing salt layer 108 both are arranged on the top of the electrodes layer 103a, 103b and 103c.

Figure 7F:
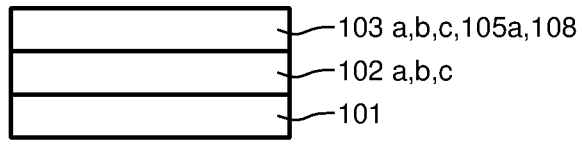
FIG. 7(f) is a schematic cross-sectional view of the electrochemically active device of the present invention, where receptor layer and lysing salt layer are integrated with the electrodes.

FIG. 7(f), which is a corresponding cross-sectional view depicting a substrate 101 on the surface of which conducting tracks 102a, 102b and 102c are arranged in the left half portion of the substrate 101. A 3-electrode arrangement in the left half portion of the substrate 101 with a working electrode 103a, counter electrode 103b and reference electrode 103c connected to the conducting tracks 102a, 102b and 102c. The receptor layer 105a and lysing salt layer 108 both are the integral part of the electrodes layer 103a, 103b and 103c.

Figure 7G:
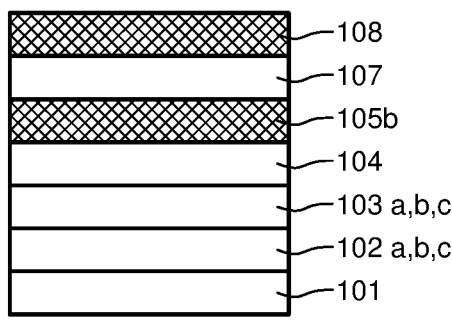
FIG. 7(g) is a schematic cross-sectional view of the electrochemically active device of the present invention, where lysing-membrane is arranged on receptor layer 105b along with lysing-membrane.

FIG. 7(g), which is a corresponding cross-sectional view depicting a substrate 101 on the surface of which conducting tracks 102a, 102b and 102c are arranged in the right half portion of the substrate 101. A 3-electrode arrangement in the right portion of the substrate 101 with a working electrode 103a, a counter electrode 103b and reference electrode 103c connected to the conducting tracks 102a, 102b and 102c. The receptor-membrane 104 is arranged on surface of the electrodes 103a, 103b and 103c. The receptor layer 105b is arranged on the surface of the receptor-membrane 104. The lysing-membrane 107 is arranged on the surface of the receptor layer 105b. The lysing salt layer 108 is arranged on the surface of the lysing-membrane 107.

Figure 7H:
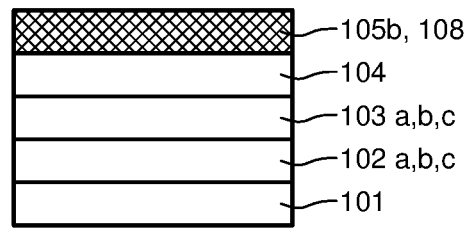
FIG. 7(h) is a schematic cross-sectional view of the electrochemically active device of the present invention, where receptor layer and lysing salt layer are arranged on receptor-membrane.

FIG. 7(h), which is a corresponding cross-sectional view depicting a substrate 101 on the surface of which conducting tracks 102a, 102b, 102c are arranged in the right half portion of the substrate 101. A 3-electrode arrangement in the right half portion of the substrate 101 with a working electrode 103a, counter electrode 103b and reference electrode 103c connected to the conducting tracks 102a, 102b, 102c. The receptor layer 105b and lysing salt layer 108 both are arranged on the receptor-membrane 104.

Figure 7I:
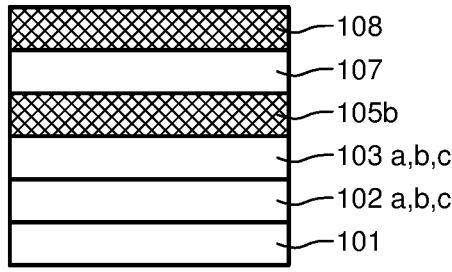
FIG. 7(i) is a schematic cross-sectional view of the electrochemically active device of the present invention, where lysing-membrane is arranged on receptor layer along with lysing-membrane and lysing salt layer.

FIG. 7(i), which is a corresponding cross-sectional view depicting a substrate 101 on the surface of which conducting tracks 102a, 102b and 102c are arranged in the right half portion of the substrate 101. A 3-electrode arrangement in the right half portion of the substrate 101 with a working electrode 103a, counter electrode 103b and reference electrode 103c connected to the conducting tracks 102a, 102b, 102c. The receptor layer 105b is arranged on surface of the electrodes 103a, 103b and 103c. The lysing-membrane 107 is arranged on the surface of the receptor layer 105b. The lysing salt layer 108 is arranged on the surface of the lysing-membrane 107.

Figure 7J:
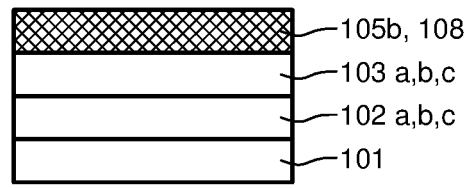
FIG. 7(j) is a schematic cross-sectional view of the electrochemically active device of the present invention, where receptor layer and lysing salt layer are arranged on the electrodes.

FIG. 7(j), which is a corresponding cross-sectional view depicting a substrate 101 on the surface of which conducting tracks 102a, 102b and 102c are arranged in the right half portion of the substrate 101. A 3-electrode arrangement in the right half portion of the substrate 101 with a working electrode 103a, counter electrode 103b and reference electrode 103c connected to the conducting tracks 102a, 102b and 102c. The receptor layer 105b and lysing salt layer 108 both are arranged on the top of the electrodes layer 103a, 103b and 103c.

Figure 7K:
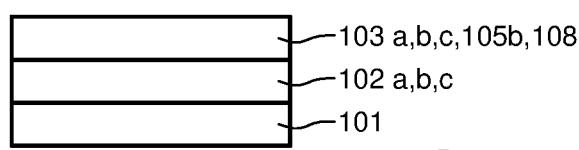
FIG. 7(k) is a schematic cross-sectional view of the electrochemically active device of the present invention, where receptor layer and lysing salt layer are integrated with the electrodes.

FIG. 7(k), which is a corresponding cross-sectional view depicting a substrate 101 on the surface of which conducting tracks 102a, 102b and 102c are arranged in the right half portion of the substrate 101. A 3-electrode arrangement in the right half portion of the substrate 101 with a working electrode 103a, counter electrode 103b and reference electrode 103c connected to the conducting tracks 102a, 102b and 102c. The receptor layer 105b and lysing salt layer 108 both are the integral part of the electrodes layer 103a, 103b and 103c.

The embodiments as shown in FIG. 7(a) (b), (c), (d), (e), (f),(g),(h),(i),(j) and (k) are used to measure the percentage methaemoglobin (% MetHb) bioanalyte in blood samples.

As shown in FIG. 8 (a), depicts a top view of the electrochemically active device with three-electrode system for Myoglobin detection.

FIG. 8 (b), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor-membrane 104 is arranged on surface of the electrodes 103a, 103b and 103c. The receptor layer 105 is arranged on the surface of the receptor-membrane 104.

Figure 8A:
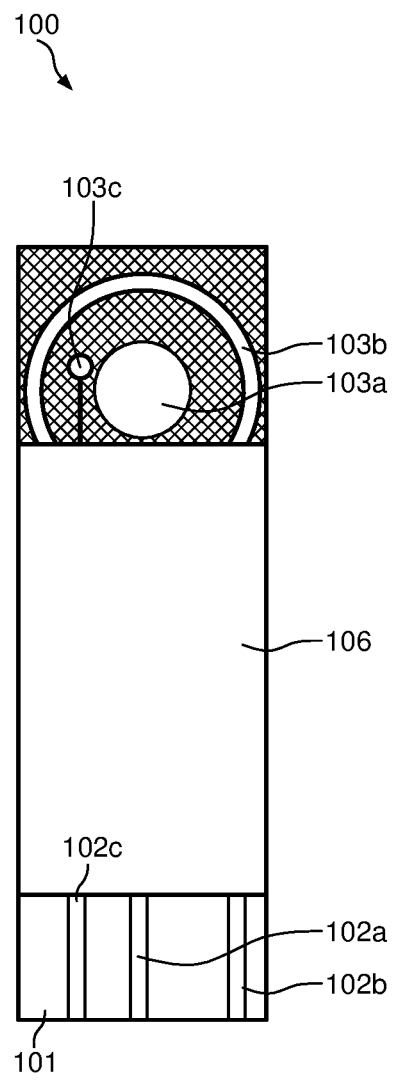
FIG. 8(a) is schematic top view of the electrochemically active device of the present invention with a three-electrode arrangement for myoglobin measurement.
Figure 8B:
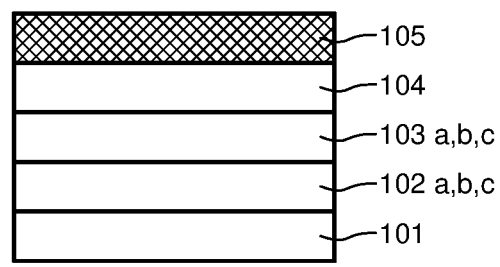
FIG. 8(b) is a schematic cross-sectional view of the electrochemically active device of the present invention, where receptor-membrane is arranged on the electrodes and receptor layer is arranged on the receptor-membrane.
Figure 8C:
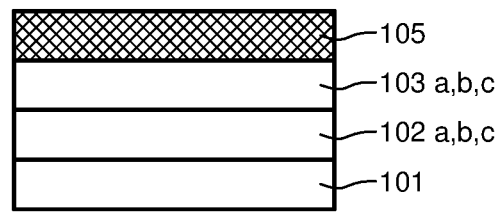
FIG. 8(c) is a schematic cross-sectional view of the electrochemically active device of the present invention, where receptor layer is arranged on the electrodes.

FIG. 8(c), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b and 102c. The receptor layer 105 is arranged on surface of the electrodes 103a, 103b and 103c.

Figure 8D:
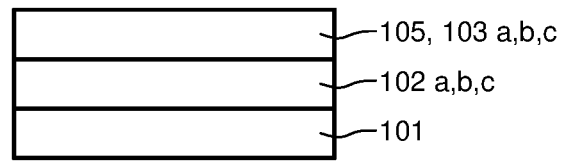
FIG. 8(d) is a schematic cross-sectional view of the electrochemically active device of the present invention, where receptor layer is integrated with the electrodes.

FIG. 8(d), which is a corresponding cross-sectional view depicting a substrate 101 on the surface of which conducting tracks 102a, 102b and 102c are arranged. A 3-electrode arrangement with a working electrode 103a, counter electrode 103b and reference electrode 103c connected to the conducting tracks 102a, 102b, 102c. The receptor layer 105 is the integral part of the electrodes layer 103a, 103b and 103c.

The embodiments as shown in FIG. 8 (a) (b), (c) and (d) are used to measure the myoglobin bioanalyte in blood samples.

Accordingly, the present invention provides an electrochemically active device for collecting and retaining a blood sample, comprising at least a pair of conductive tracks disposed on a substrate. At least a two-electrode member connected to the conductive tracks. The device is provided with a receptor with an integral receptor-membrane and arranged on the electrode member. A lysing agent is arranged in chemical contact with a receptor to receive the blood sample and release electrochemically active heamoglobin bioanalyte and its complexes from red blood cells (RBC) of the blood sample. The receptor is arranged on the two-electrode member, to receive the non-electrochemically active heamoglobin bioanalyte and its complexes and convert the non-electrochemically active heamoglobin bioanalyte and its complexes, into an electrochemically active bioanalyte and its electrochemically active complexes. In an alternate embodiment, the receptor is disposed directly on said at least two-electrode member, without the receptor-membrane.

The device of the present invention is disposed in a housing, where the housing is a cartridge or a cassette.

Figure 9:
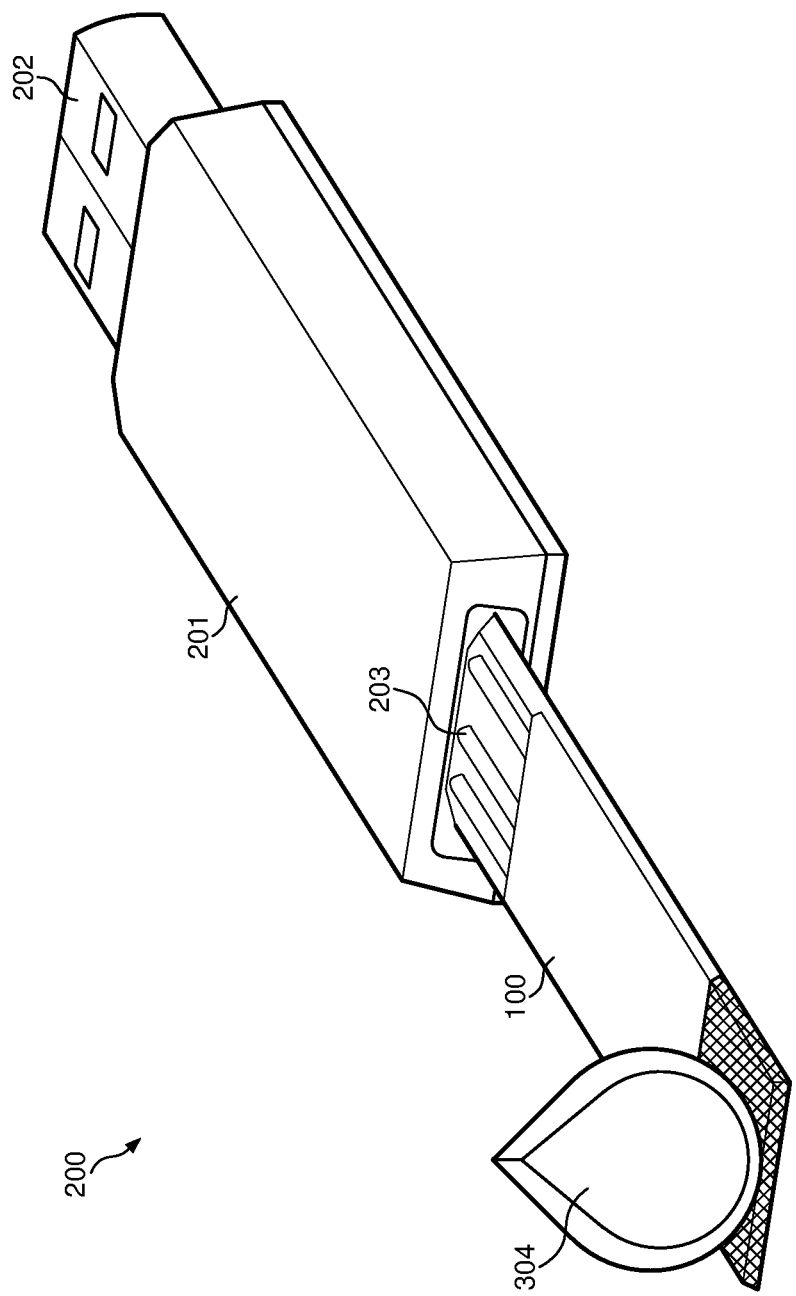
FIG. 9 is a perspective view of the device holder of the present invention holding the electrochemically device and adapted to receive the desired blood sample with haemoglobin bioanalyte and its complexes.

Hitherto, illustrative embodiments of the electrochemically active device Now, the illustrative embodiments of the device holder holding the electrochemically active device is described by referring to FIG. 9. The device holder 200 for sensing a bioanalyte in a blood sample, comprises a housing 201 with device detection and internal circuitry and the housing 201. The device holder 210 is adapted to connect to preferably an external processor having a display member. A device insertion port 203 is provided in the housing 201. The device 100, of the present invention, which is permitted to pass through the device insertion port 203 is arranged to receive the desired blood sample in reduced volume. A USB plug 202 is connected to the housing 201 as shown in FIG. 9. The device holder 200 is used to collect and retain the biological sample for subsequent testing. The device holder 200 is also provided with device detection, data storage, signal conditioning and data acquisition features to identify the type of bioanalyte that is stored on the device 100. The device holder 200 enables the user to insert the holder 200 into a biosensor and collect the biological sample for measurement.

Therefore, the present invention provides a device holder 200 for holding the electrochemically active device 100 with a desired blood sample. The device holder 200 is with the device detection and signal conditioning circuitry, which is arranged in the housing 201. USB connector 202 is arranged at one end of the housing 201 and an electrically conductive port 203 at the other end of the housing 201. The electrochemically active device 100 for collecting and retaining a blood sample is connected to the device holder 200, through the electrically conducting port 203. The device 100 is provided with a minimum pair of conductive tracks 102a and 102b, which are patterned or arranged on the substrate 101. The two-electrode member 103a and 103b is connected to the pair of conductive tracks 102a and 102b. The receptor 104 is integrated with receptor-membrane 105 and arranged on the two-electrode member 103a and 103b. The lysing agent is in chemical connection with the receptor 104 to receive the blood sample and release electrochemically active heamoglobin bioanalyte and its complexes from red blood cells (RBC) of the blood sample. In this arrangement the receptor 104 is arranged to receive the non-electrochemically active heamoglobin bioanalyte and its complexes and to convert the non-electrochemically active heamoglobin bioanalyte and its complexes, into an electrochemically active bioanalyte and electrochemical complexes.

The device holder 200 of the present invention is powered on after inserting into a processor having a display unit. The device is then loaded into the device holder 200. The device detection circuitry means or circuitry arranged inside the housing 200 is adapted to detect the designated device. When the device holder 200 detects the device, the device 100 is then loaded with the biological sample and a desired redox potential is applied by the internal circuitry in the digital-to-analog converter (DAC) to the working electrode of the device 100 with respect to the reference electrode. The redox current that is passing through the counter and working electrodes is measured by internal circuitry by using I to V converter.

Figure 10A:
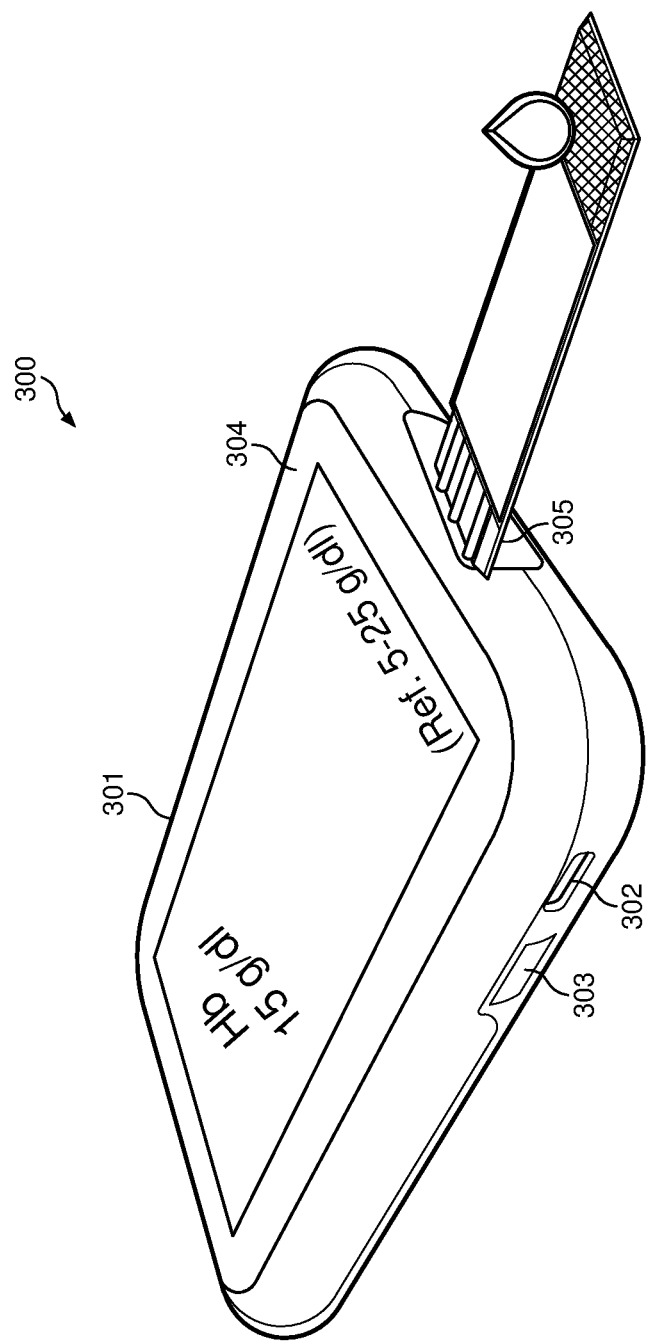
FIG. 10(a) is a perspective view of point-of-care biosensor holding the device of the present invention for quantitative measurement and display of haemoglobin bioanalyte and its complexes.

The point-of-care biosensor 300 for sensing a bioanalyte in a biological sample, as shown in FIG. 10(a), the biosensor comprises a housing 301. A micro USB 302 and micro SD card 303, which are arranged on the housing 300. The micro USB 302 is used to charge the biosensor 300 and micro SD card is used as a storage device. The housing 301 is also provided with display member 304, which can be an LCD, LED, OLED, OMLED, TFT or any other such display devices, including touch-sensitive devices. A device insertion port 305 is provided in the housing 301. The device insertion port 305 is provided with a metallic contacts to engage the device electrically. In other words, the insertion port 305 is provided to receive the device 100, through the electrode members of the device 100. The point-of-care biosensor 300 is provided to facilitate a user to use the device 100, in a simple way, along with the point-of-care biosensor 300. The device 100 is initially inserted into the loaded point-of-care biosensor 300 and loaded with a selected biological sample, in reduced volume, in the range of 1-300 µL, which entails a minimum invasive means in collecting the biological sample. The user is also at liberty to use the biosensor 300 at a room temperature and without concerning about other environmental factors such as humidity, temperature variation and storage conditions. The user by using the biosensor 300 is able to measure the concentration levels of the desired bioanalytes, in a substantially shorter period of time, since the bioanalyte binds the receptor, instantaneously. The user is provided with an instantaneous and accurate display of the concentration of the bioanalyte on the display member 304, since the inherent binding nature of bioanalyte is used in the biosensor 300 to measure the concentration levels. By using the biosensor 300 of the present invention, the user is enabled to use the biosensor without a need for active preparation of the biological sample before it is tested.

Figure 10B:
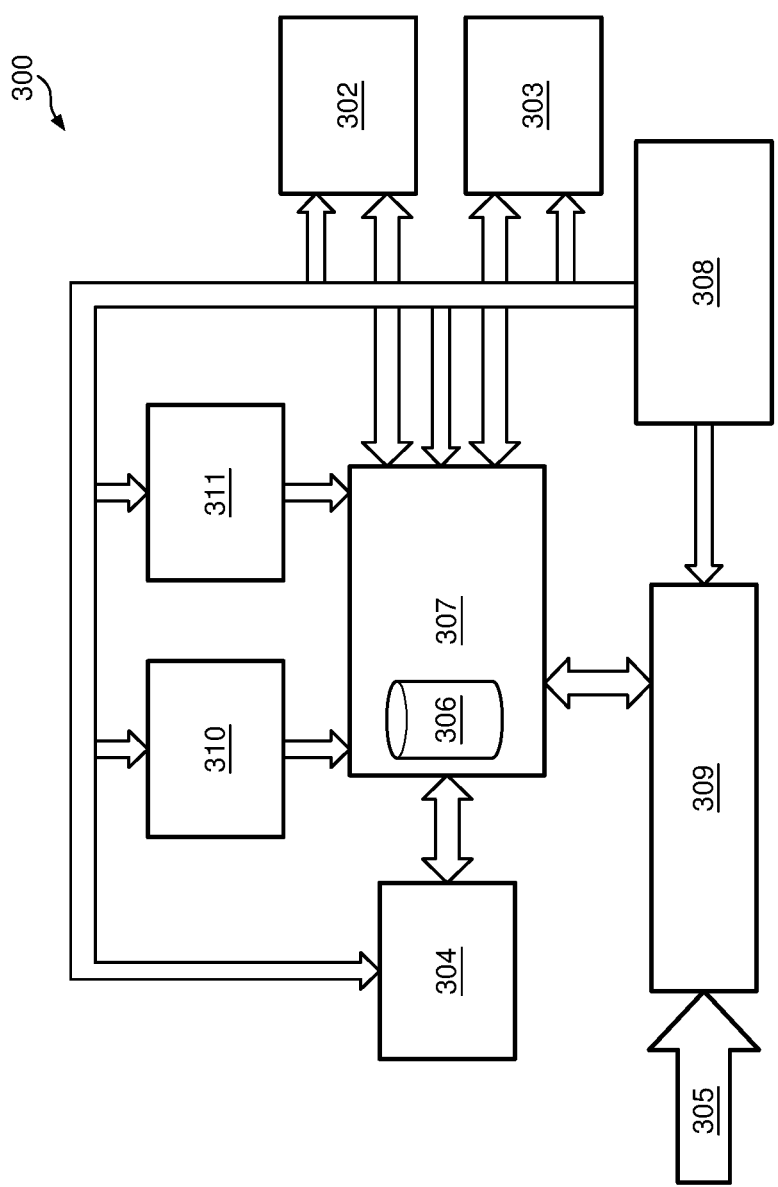
FIG. 10(b) is a schematic depiction of a broad internal electronic architecture of the point-of-care biosensor of the present invention.

Now, referring to FIG. 10(b), an internal electronic hardware architecture of the point-of-care biosensor 300 is described. A database member 306 is provided in the housing 301 to store standard values of redox current and bioanalyte concentration of haemoglobin (Hb), glycated haemoglobin (GHb), methaemoglobin (MetHb) and myoglobin, present in the blood samples. The database 306 also incorporates the data pertaining to historical and current data of concentrations of the bioanalytes. The executables that are required to perform the various functions of the biosensor 300 are stored on a medium of the point-of-care biosensor 300. A digital controller 307 is provided in the housing 301 and connected to the database member 306 and configured to apply a redox potential to at least a two-electrode member having an electrochemically active receptor with a blood sample having haemoglobin and its complexes and to measure the corresponding redox current. The digital controller 307 is arranged to measure a redox current of the haemoglobin bioanalyte and its complexes by linearly matching with the value of concentration and display the value of measured concentrations of the heamoglobin bioanalyte and its complexes.

A power supply to the point-of-care biosensor 300 is regulated by a power supply unit 308, which is connected to the biosensor 300. The power supply unit 308 includes both online and offline rechargeable battery with charging circuitry. A signal conditioning and device detection unit 309 is connected to the microcontroller 307 to detect the presence of the device 100 in the point-of-care biosensor 300 and to apply the redox potential to the electrodes and measuring the redox current from the selected biological sample. Humidity and temperature sensors 310 and 311 are arranged in the housing 301. Once the measurement of the concentration levels of the bioanalyte is completed by the microcontroller 307, the concentration levels are displayed on the display member 304, along with historical data of the concentration levels of the desired bioanalyte.

Therefore, the point-of-care biosensor for measuring a concentration of a bioanalyte in a blood sample comprises 301 with display member and the electrically conducting port. The electrochemically active device 100 for collecting and retaining a blood sample is connected to the device holder 200, through the electrically conducting port 203. The device 100 is provided with a minimum pair of conductive tracks 102a and 102b, which are patterned or arranged on the substrate 101. The two-electrode member 103a and 103b is connected to the pair of conductive tracks 102a and 102b. The receptor 104 is integrated with receptor-membrane 105 and arranged on the two-electrode member 103a and 103b. The lysing agent is in chemical connection with the receptor 104 to receive the blood sample and release electrochemically active heamoglobin bioanalyte and its complexes from red blood cells (RBC) of the blood sample. In this arrangement the receptor 104 is arranged to receive the non-electrochemically active heamoglobin bioanalyte and its complexes and to convert the non-electrochemically active heamoglobin bioanalyte and its complexes, into an electrochemically active bioanalyte and electrochemical complexes. The digital controller that is arranged in housing and configured to apply a redox potential and measure redox current from the device. The digital controller is also configured to retrieve and display concentration levels of haemoglobin and its complexes, by linearly matching the concentrations of haemoglobin and its complexes thereof. The database member of The point-of-care biosensor, is arranged to store standard values of concentrations haemoglobin bioanalyte and its complexes in blood samples along with reciprocal redox currents is connected to the digital controller.

The present invention also provides a method for an accurate detection and quantitative measurement of haemoglobin bioanalyte and its complexes in a blood sample. The desired blood sample is collected in very small volumes i.e., in the range of micro litres GO, from human subjects, with a minimally invasive means, by following standard protocols. In the method of present invention the preferred volume of the biological sample that can be used for the measurement of bioanalyte is preferably in the range of 1-300 microlitres ($\mu L$). The required volume of the sample is subject to the size of the surface area of the receptor of the device. The reduced collection of sample substantially reduces trauma in the subjects, since it is obtained through a minimally invasive sample extraction technique. The reduced volume of biological samples also avoids the need for a user to source for phlebotomy collection products.

In the method of the present invention, the determination and accurate measurement of a bioanalyte, is performed by implementing the principle of electrochemistry. Accordingly, the bioanalyte that is advantageously selected for its measurement is a globular protein-haemoglobin (Hb), glycated haemoglobin (GHb), methaemoglobin (MetHb) and myoglobin, through a measurement of redox current flowing through electrochemically-active devices, on the application of an electric potential.

In the method of present invention the receptor substance is prepared, advantageously as a solution of preferred chemical substances as hereinafter described. For instance, in case pyridine and NaOH is selected as a preferred receptor, NaOH is dissolved preferably in distilled water or any other solvents which can dissolve these substances.

In case of a receptor substance, which is based imidazole, is preferably dissolved in distilled water, or any other solvents which can dissolve these substances.

In the event methylene blue (MB) is used as a receptor, the chemical substance is preferably dissolved in distilled water or any other solvents, which can dissolve this chemical substance.

In the event methylene blue (MB) and oxidizing agent preferably $NaNO_2$ is used as a receptor, the chemical substance is preferably dissolved in distilled water or any other solvents, which can dissolve this chemical substance.

In the event inorganic substance preferably NaOH is used as a receptor, the chemical substance is preferably dissolved in distilled water or any other solvents, which can dissolve this chemical substance.

The receptor solution thus prepared is applied to the electrode members or membranes of the device of the present invention, prior to the application of biological samples.

Alternately, the receptor solution thus prepared is applied to the electrode members or membranes of the device and dry it on the surface to form a chemical layer of the present invention, prior to the application of biological samples.

Alternately, the receptor solution can also be premixed with the biological samples and the mixed solution is applied to the electrode members or membranes of the device.

Accordingly, the receptor substance can be an organic or an inorganic substance or a combination of these substances.

In yet another aspect of the present invention, the organic substance is selected from the group consisting of heterocyclic organic substances with N-heteroatom, preferably, pyridine, pyridine HCl, hydroxypyridine, cyano pyridine, imidazole, pyrazole, indole, pyramidine, purine, more preferably, pyridine and imidazole.

In further another aspect of the present invention a method for the detection and measurement of heamoglobin is now described. In order to test the presence of heamoglobin in a blood sample, the reduced volume of the biological sample (blood) is brought in chemical contact with the receptor of the device of the present invention.

The structure of haemoglobin attracts the researchers for electrochemical detection of this molecule. Haemoglobin contains four iron with oxidation state +2 in its structure but in its native form, this iron is embedded deep in the globin chains and not available for the participate in electrochemical reaction.

Figure 11:
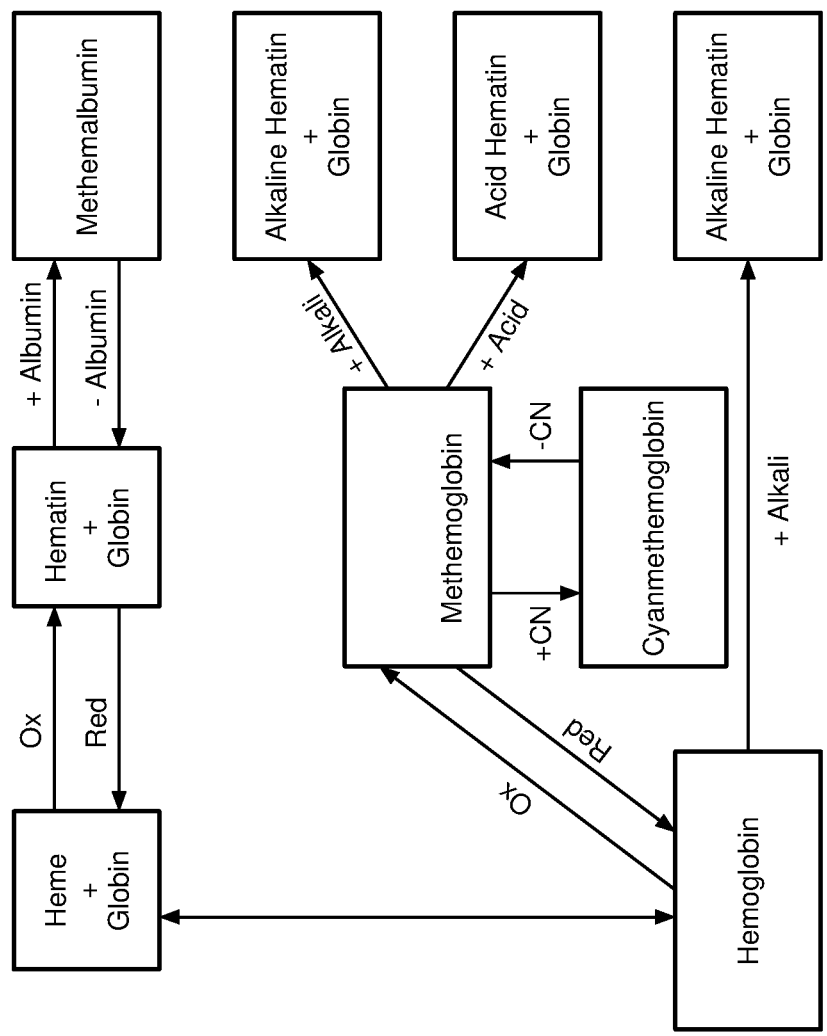
FIG. 11 is a schematic depiction of redox reactions of haemoglobin.
Figure 12:
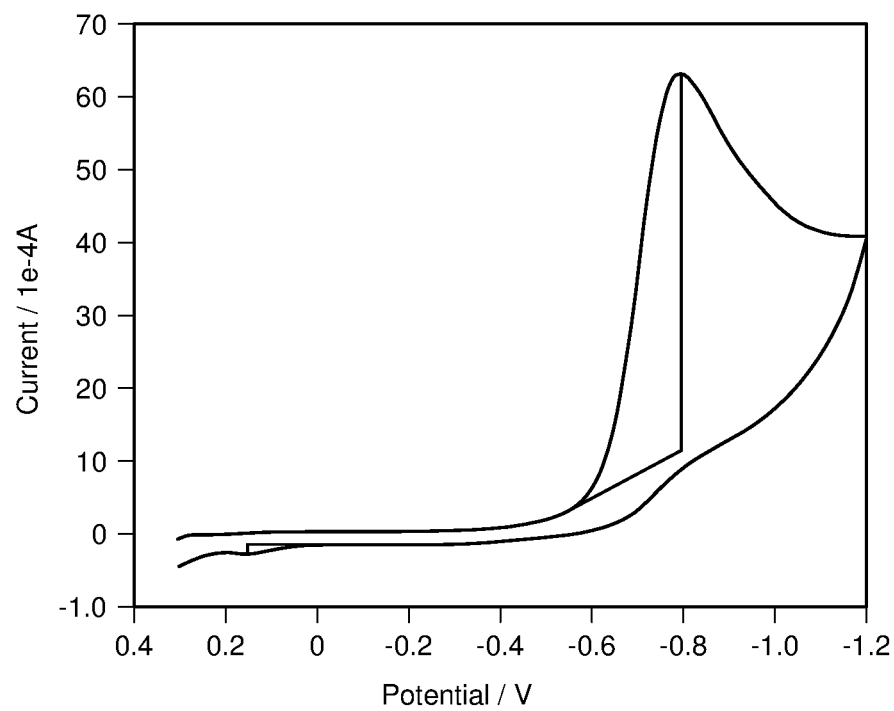
FIG. 12 is a cyclic voltammogram of haemoglobin subsequent to conversion into alkaline hematin in blood sample.
Figure 13A:
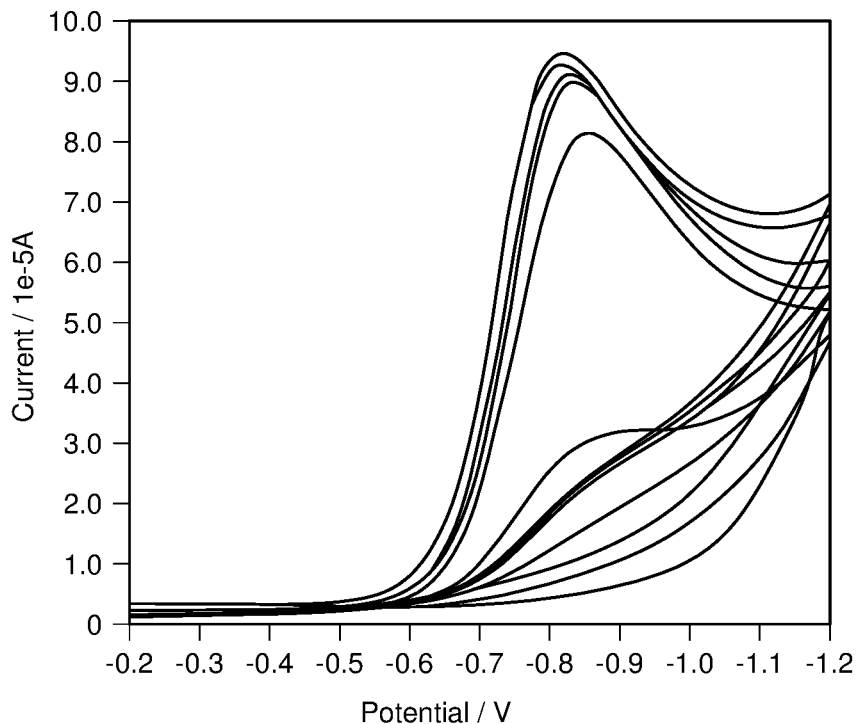
FIG. 13(a) is a cyclic voltammogram of haemoglobin after its conversion into alkaline hematin at varying concentrations.
Figure 13B:
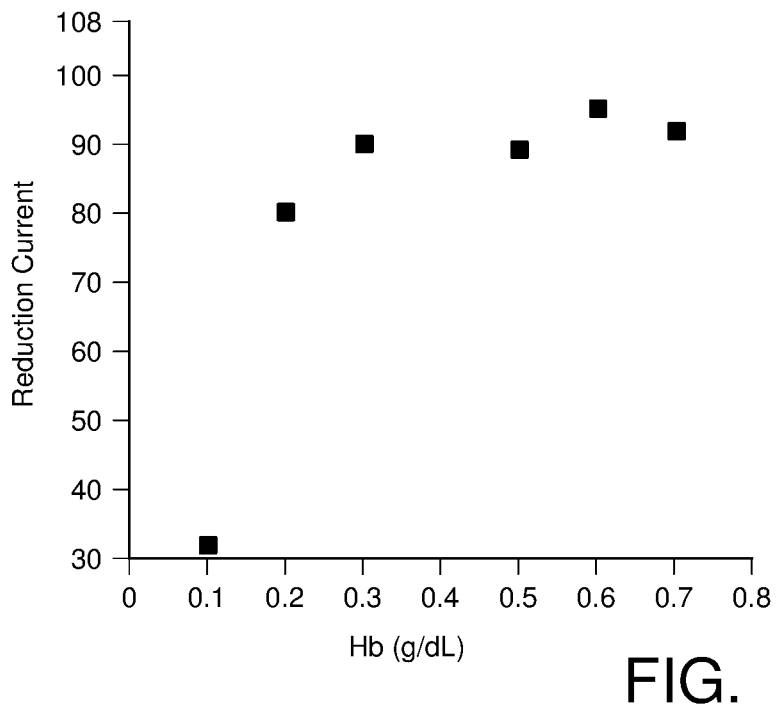
FIG. 13(b) is a plot depicting reduction current Vs haemoglobin at varying concentrations of haemoglobin.

Haemoglobin shows the different oxidation states of iron depending on the conditions of the solution as shown in FIG. 11. Under alkaline conditions, haemoglobin can be converted into alkaline hematin by separation of globin part. Hematin is the oxidized form of heme prosthetic group in haemoglobin structure. Hematin is relatively small molecule and can communicate with electrode surface more easily than haemoglobin molecule. Hematin gives the reduction peak in cyclic voltammetry as shown in FIG. 12. However, hematin shows the good reduction peak, but alkaline hematin method for electrochemical detection of total haemoglobin is not preferred. The reduction current response of alkaline hematin based electrochemical detection of haemoglobin is not linear and this is due to the fact that in alkaline solution, hematin form dimers and adsorbed at the electrode surface, thus blocking any charge transfer at electrode interface. So it is difficult to get the repeatable linear response, as shown in FIG. 13(a) and FIG. 13(b). Hematin in the aqueous solution gives the irreversible reduction peak. After adsorption, it is very difficult to get the linear current response.

In one aspect of present innovation the receptor for haemoglobin detection is pyridine and NaOH.

Figure 14A:
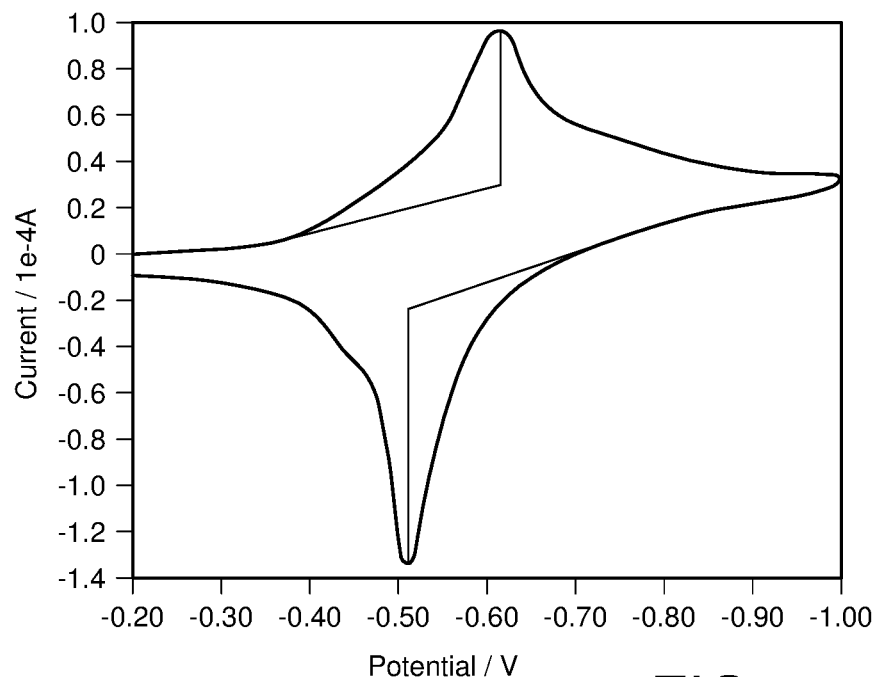
FIGS. 14(a) and (b) depict cyclic voltammograms of nitrogen base complexes with haemoglobin in the presence of imidazole and pyridine HCl.
Figure 14B:
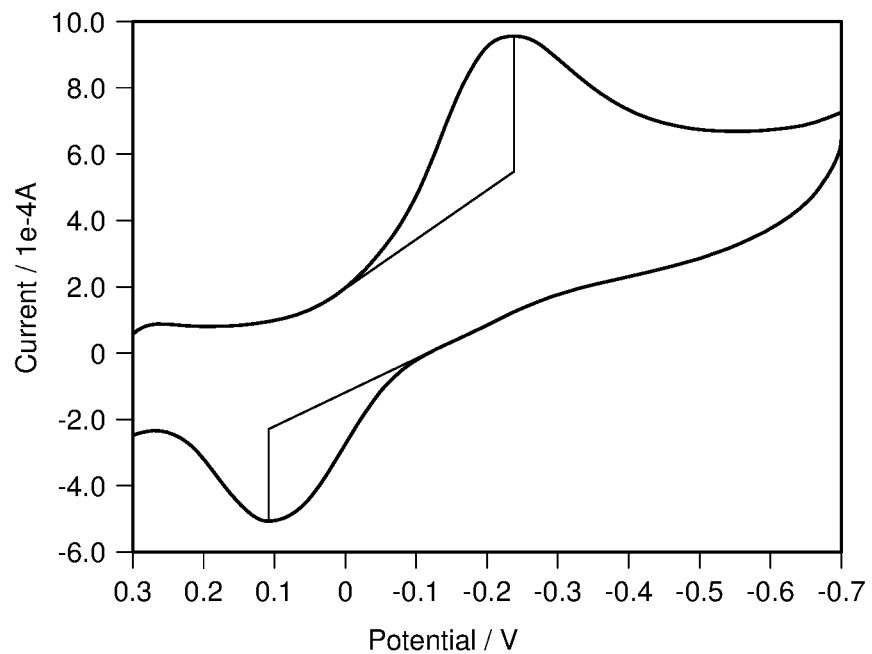
Figure 15:
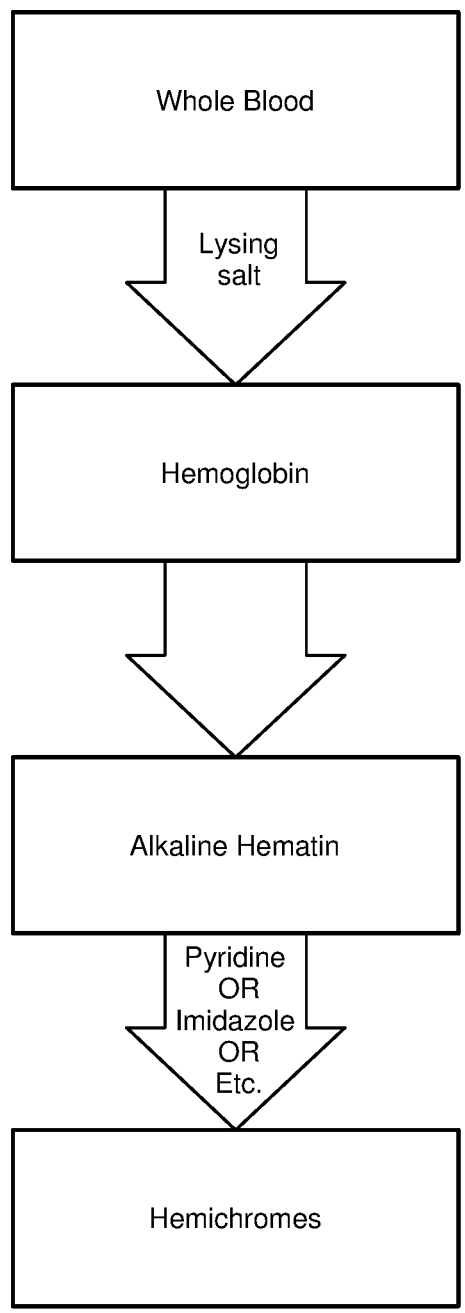
FIG. 15 is a flowchart depicting process steps for the conversion of whole blood into hemichromes.

The porphyrin ring of hematin satisfies the four X-Y coordination positions of the ferric iron. The two remaining coordination positions are located perpendicularly above and below the ferric on the Z-axis. When these positions on the Z-axis are occupied by $\pi$-bonding ligands such as pyridine, imidazole, cyanide or other heterocyclic chemicals with N-heteroatom and form a coordinated complex, these complexes are also designated hemichromes. Hemichrome forms with the coordination of nitrogen base of heterocyclic reagent and gives the reversible redox peaks in cyclic voltammetry experiments, as shown in FIGS. 14(a) and (b). The flowchart of pyridine hemichrome formation is summarized in FIG. 15.

In view of converting the non-electrochemically active haemoglobin into electrochemically active pyridine hemichrome, pyridine and NaOH are selected as a ligand receptor, to detect haemoglobin concentration. The peak redox current values of pyridine hemichrome are used to compare the variance in the haemoglobin concentration in blood sample.

Prior to the measurement of haemoglobin concentration in desired blood sample. Data pertaining to standard haemoglobin concentrations (g/dL) in various human blood samples are collected and stored in a database member. Thus the database member is populated with the values of standard haemoglobin concentrations (g/dL) along with the corresponding redox current values ($\mu$A) of pyridine hemichrome. The preferred redox current values for the designated concentrations are obtained in an iterative manner, where repeated tests, result in identical redox current values, for the selected haemoglobin concentration.

The measured redox current is matched with the stored redox current values and the matching haemoglobin concentration is secured and displayed by the biosensor. Alternately, the linear-fit equation can also be used to compute the concentration of bioanalyte by using the redox current value. The biosensor after having extracted the value of concentration of haemoglobin in the blood sample displays the value.

Figure 16:
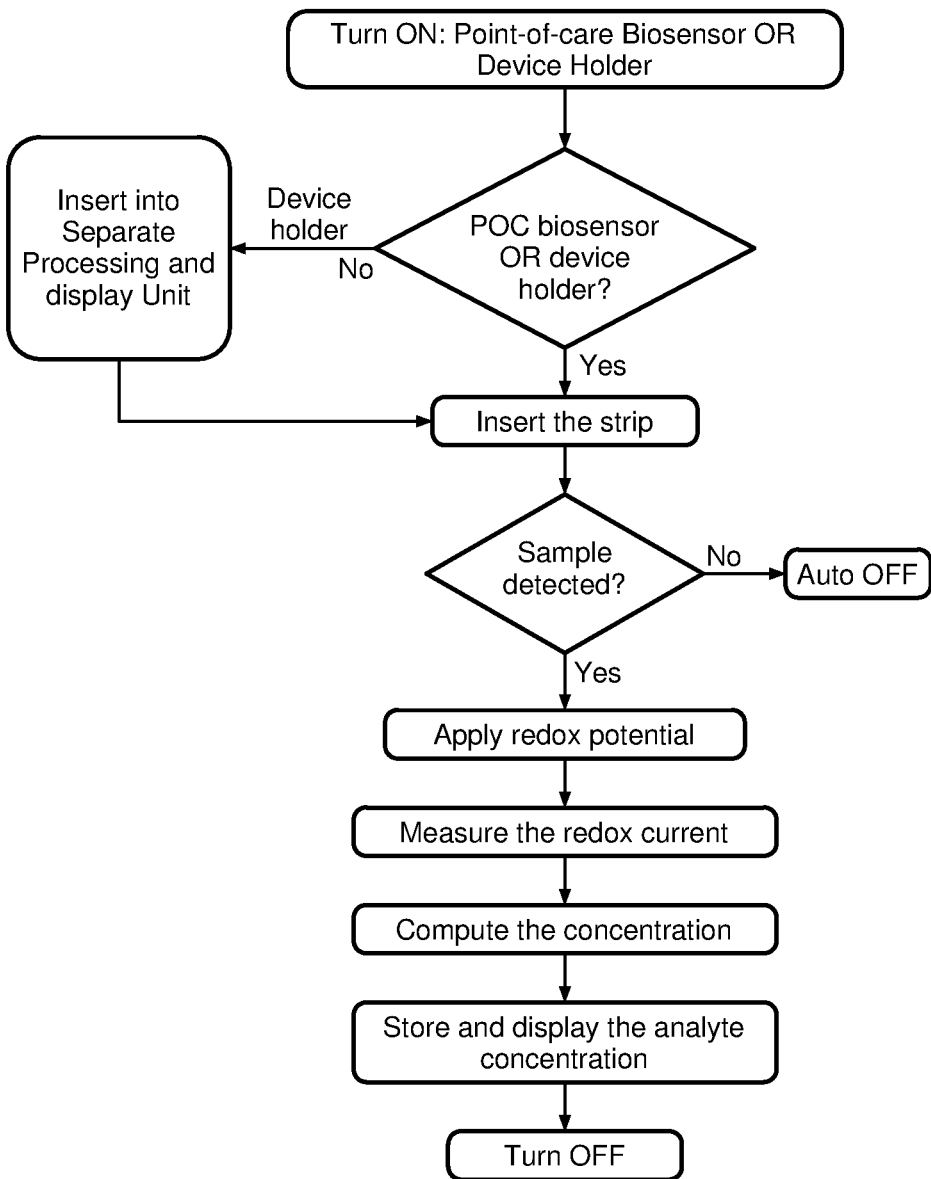
FIG. 16 is a high-level flow chart depicting process steps to measure quantitatively the concentration of the Hb bioanalyte by using the device and point-of-care biosensor of the present invention.

Now, process steps of the measurement of bioanalyte are described by referring FIG. 16. The biosensor of the present invention is selected and powered on. The device is then loaded into the biosensor. The biosensor is adapted to indicate to detect the designated device. When the device is detected by the biosensor the device is loaded with the biological sample and a desired redox potential is applied by digital-to-analog converter (DAC) to the working electrode of the device with respect to the reference electrode. Redox potential is a measure of the tendency of a chemical substance to acquire electrons and thereby be reduced. Each chemical substance has its own intrinsic redox potential. The more positive the potential, the greater is the substance affinity for electrons and the tendency to be reduced. The redox current that is passing through the counter and working electrodes is measured by using I to V converter.

The measured redox current is matched with the stored redox current values and the matching haemoglobin concentration is secured and displayed by the biosensor. Alternately, the linear-fit equation can also be used to compute the concentration of bioanalyte by using the redox current value. The biosensor after having extracted the value of concentration of haemoglobin in the blood sample displays the value.

In another aspect of the method of the present invention, Imidazole is adopted as a receptor and SDS is used as a lysing and oxidizing agent, to form Imidazole-methaemoglobin complex. SDS lyses the RBCs and converts the haemoglobin molecule in to methaemoglobin molecule in which the oxidation state of iron is +3. The N-heteroatom of the Imidazole coordinates with this iron and form the Imidazole-methaemoglobin complex, which shows the reversible CV. In view of coordination of imidazole to methaemoglobin exhibiting a reduction and oxidation current peak, Imidazole is selected as a receptor, to detect haemoglobin concentration.

In view of converting the non-electrochemically active haemoglobin into electrochemically active Imidazole-methaemoglobin complex, Imidazole and/or an oxidizing agent is selected as a ligand receptor, to detect haemoglobin concentration. The peak redox current of imidazole-methaemoglobin complex is used to compare the variance in the haemoglobin value.

Prior to the measurement of haemoglobin concentration in desired blood sample. Data pertaining to standard haemoglobin concentrations (g/dL) in various human blood samples are collected and stored in a database member. Thus the database member is populated with the values of standard haemoglobin concentrations (g/dL) along with the corresponding redox current values ($\mu$A) of imidazole-methaemoglobin complex. The preferred redox current values for the designated concentrations are obtained in an iterative manner, where repeated tests, result in identical redox current values, for the selected haemoglobin concentration.

The measured redox current is matched with the stored redox current values and the matching haemoglobin concentration is secured and displayed by the biosensor. Alternately, the linear-fit equation can also be used to compute the concentration of bioanalyte by using the redox current value. The biosensor after having extracted the value of concentration of haemoglobin in the blood sample displays the value.

In a further aspect of the present invention, the concentration of glycated haemoglobin is determined by using the biosensor of the present invention. The biosensor thus used is advantageously provided with an electrode configuration as shown FIG. 5 (a). Each of two sets of electrodes is treated with Imidazole and lysing agent. One of the sets of electrodes is provided with a membrane treated with boronic acids or their derivatives.

Boronic acids and boronic acids derivatives have an affinity towards carbohydrates such as glucose, glycated proteins such as glycated haemoglobin. In the present invention boronic acids affinity principle (or Boronate affinity principle) is used to separate the glycated haemoglobin component from the total haemoglobin component.

Figure 17:
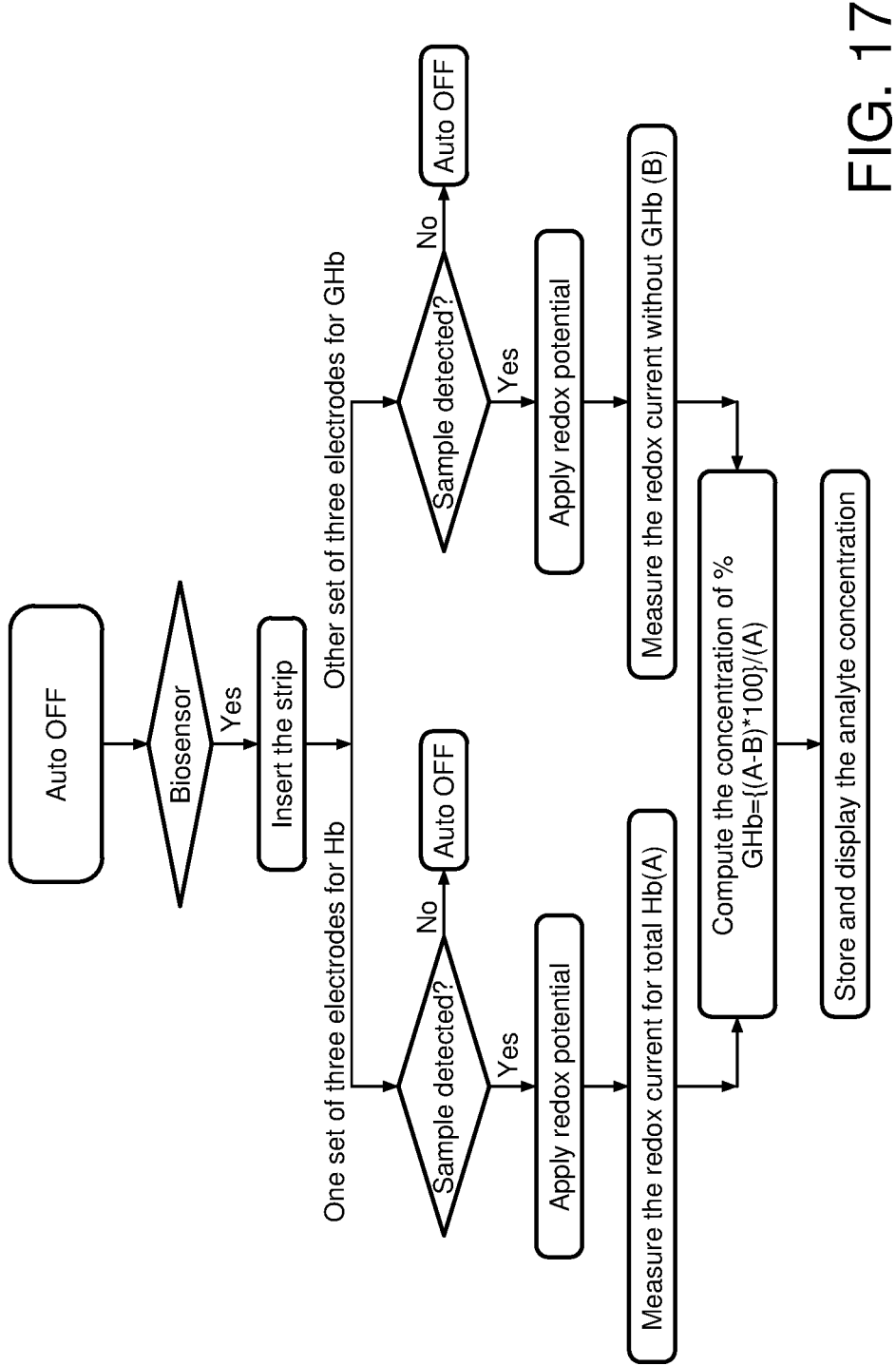
FIG. 17 is a high-level flow chart depicting process steps to measure quantitatively the concentration of the glycated Hb by using the device and point-of-care biosensor of the present invention.

A reduced quantity of blood is applied on both the sets of electrodes and process steps as shown in FIG. 17. Redox potential is applied to both the sets of the electrodes and the corresponding redox current is measured from these electrodes. By computing the difference in measured redox current in both the electrodes, the concentration of the glycated haemoglobin is obtained.

In view of converting the non-electrochemically active haemoglobin into electrochemically active Imidazole-methaemoglobin complex, Imidazole and/or an oxidizing agent is selected as a ligand receptor, to detect total haemoglobin and haemoglobin concentration without glycated haemoglobin component. The difference of these two components is used to calculate the percentage of glycated haemoglobin (% GHb). The peak redox current of imidazole-methaemoglobin complex is used to compare the variance glycated haemoglobin in the blood sample.

Prior to the measurement of haemoglobin concentration in desired blood sample. Data pertaining to standard haemoglobin concentrations (g/dL) in various human blood samples are collected and stored in a database member. Thus the database member is populated with the values of standard haemoglobin concentrations (g/dL) along with the corresponding redox current values (µA) of imidazole-methaemoglobin complex. The preferred redox current values for the designated concentrations are obtained in an iterative manner, where repeated tests, result in identical redox current values, for the selected haemoglobin concentration.

The measured redox current is matched with the stored redox current values and the matching haemoglobin concentration is secured and displayed by the biosensor. Alternately, the linear-fit equation can also be used to compute the concentration of bioanalyte by using the redox current value. The biosensor after having the redox current values, computes the percentage glycated haemoglobin value and displays the value.

Figure 18:
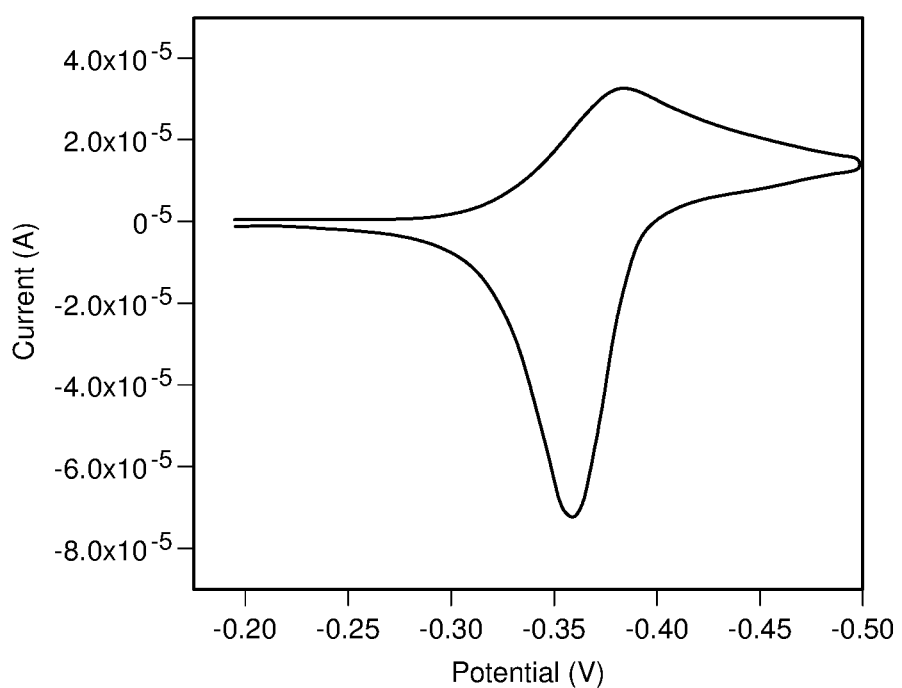
FIG. 18 is a cyclic voltammogram of methylene blue.
Figure 19:
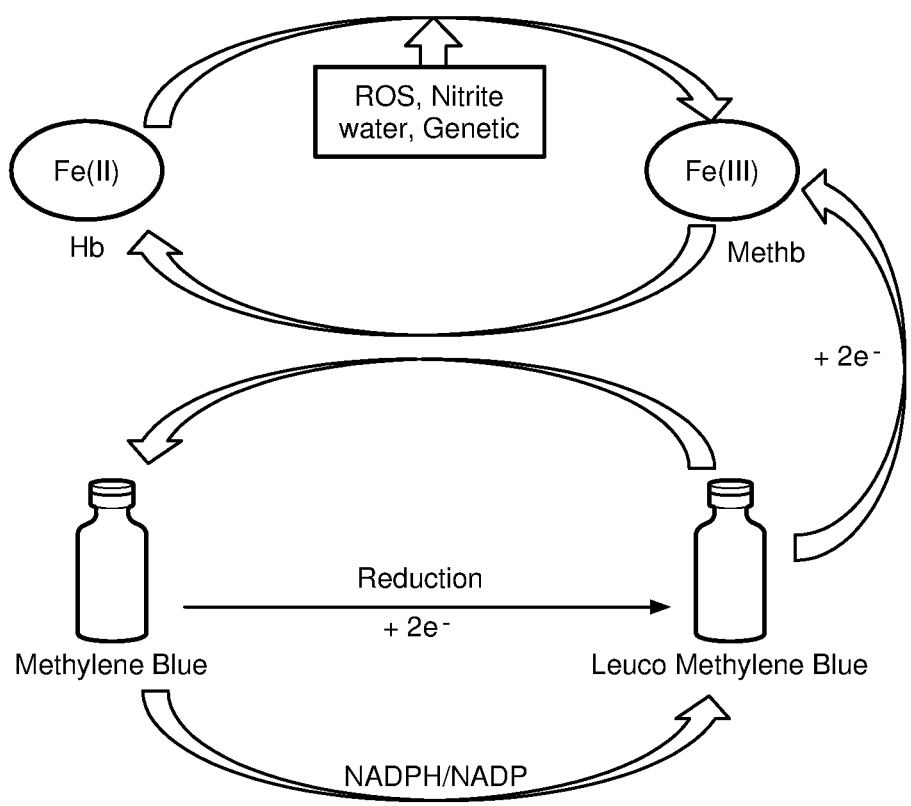
FIG. 19 is a schematic depiction of redox behaviour of methylene blue in methaemoglobinaemia.

Methylene blue (MB) is a well-known electrochemical redox-dye. MB demonstrates a reversible redox peaks in cyclic voltammogram as shown in FIG. 18. MB is commonly used in biology for DNA staining and as an antidote for methaemoglobinaemia disorder. In methaemoglobinaemia treatment, MB reduces (by gaining electrons) into leucomethyleneblue (LMB), in the presence of nicotinamide adenine dinucleotide phosphate (NADPH) enzyme. Thereafter, LMB donates its electron to the ferric form ($Fe^{+3}$) of iron in methaemoglobin molecule and converts it back into ferrous form ($Fe^{+2}$) in haemoglobin molecule. The reduction of MB into LMB in the presence of NADPH enzyme is the key to this process as shown in FIG. 19. In the present invention, MB is reduced into LMB by electrochemical route using cyclic voltammetry technique. If any $Fe^{+3}$ containing element or an elemental ferric iron is added in the reduced form of the MB (LMB), then MB donates its electron to ferric form ($Fe^{+3}$) and reduces it into ferrous form of iron ($Fe^{+2}$). In this reaction, LMB is further oxidized into MB form while Iron in $Fe^{+3}$ form reduced into Iron $Fe^{+2}$ form, as shown in the following reaction:

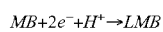

$$MB + 2e^- + H^+ \rightarrow LMB$$

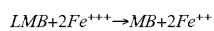

$$LMB + 2Fe^{+++} \rightarrow MB + 2Fe^{++}$$

In yet another aspect of the present invention the receptor for methaemoglobin detection is methylene blue (MB).

The reduction current peak of MB increases after adding the methaemoglobin because of catalytic current flow due to the donation of electrons from LMB to $Fe^{+3}$ Based on aforementioned principle of activity of methaemoglobin with MB, in the method of present invention MB based receptor is adopted for methaemoglobin detection. The biosensor thus used is advantageously provided with an electrode configuration as shown FIG. 6. The measured redox current is matched with the stored redox current values and the matching methaemoglobin concentration is secured and displayed by the biosensor. Alternately, the linear-fit equation can also be used to compute the concentration of bioanalyte by using the redox current value. The biosensor after having extracted the value of concentration of methaemoglobin in the blood sample displays the value.

In one aspect of present innovation for percentage of methaemoglobin (% MetHb) detection out of the total haemoglobin (Hb), a combination of methylene blue (MB) and Imidazole is used as a receptor.

In a further aspect of the present invention, the percentage of methaemoglobin (% MetHb) is determined by using the biosensor of the present invention. The biosensor thus used is advantageously provided with an electrode configuration as shown FIG. 7 (a). One of two sets of electrodes is treated with Imidazole and lysing agent. Other set of electrodes is provided with MB.

Figure 20:
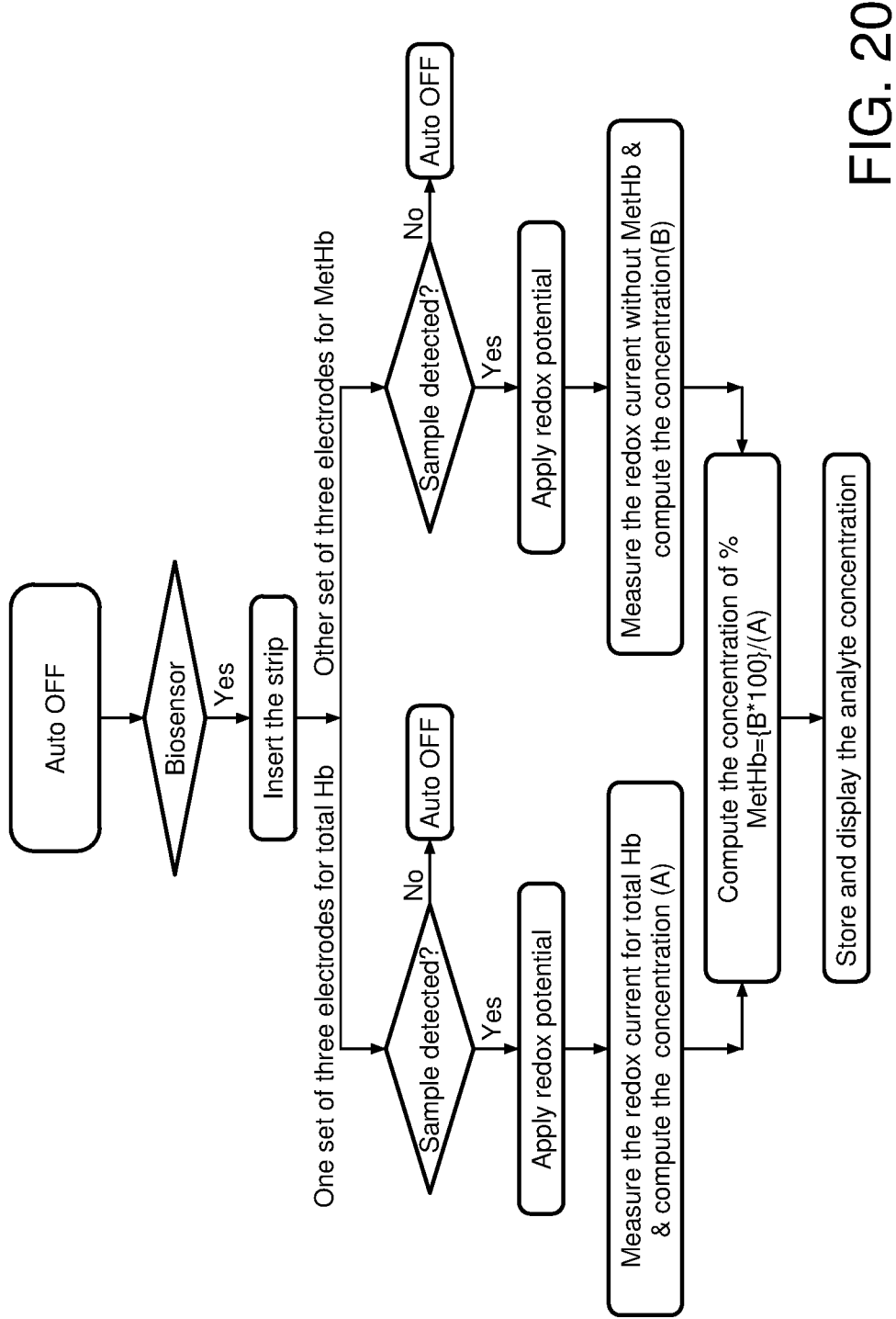
FIG. 20 is a high-level flow chart depicting process steps to measure quantitatively the concentration of MetHb in blood sample.

A reduced quantity of blood or blood plasma is applied on both the sets of electrodes and process steps as shown in FIG. 20. Redox potential is applied to both the sets of the electrodes and the corresponding redox current is measured from these electrodes. By computing the difference in measured concentrations in both the electrodes, the concentration of the percentage MetHb is obtained.

Prior to the measurement of % MetHb in desired blood sample. Data pertaining to standard haemoglobin concentrations (g/dL) and standard methaemoglobin concentrations in various human blood samples are collected and stored in a database member. Thus the database member is populated with the values of standard haemoglobin and methaemoglobin concentrations (g/dL) along with the corresponding redox current values. The preferred redox current values for the designated concentrations are obtained in an iterative manner, where repeated tests, result in identical redox current values, for the selected haemoglobin and methaemoglobin concentrations.

The measured redox current is matched with the stored redox current values and the matching haemoglobin and methaemoglobin concentrations are secured and used to compute the % MetHb. Alternately, the linear-fit equation can also be used to compute the concentration of bioanalyte by using the redox current value. The biosensor after having the redox current values, compute the percentage methaemoglobin value and displays the value.

In another aspect of present invention, a combination of MB-NaNO$_2$ receptor is used for the detection of haemoglobin. After lysing the RBCs, the oxidizing agent converts all the haemoglobin components into the methaemoglobin, which can be detected by using the methylene blue as a receptor. In case, the combination of NaNO$_2$-MB as a receptor for total haemoglobin detection then the peak reduction current increases because of the fact that when we add the methaemoglobin in the MB solution then the reduced methylene blue form (LMB) donates its electrons to the methaemoglobin complex and increases the concentration of MB at the electrode surface. The biosensor thus used is advantageously provided with an electrode configuration as shown FIG. 4 (a).

The measured redox current is matched with the stored redox current values and the matching total haemoglobin concentration is secured and displayed by the biosensor. Alternately, the linear-fit equation can also be used to compute the concentration of bioanalyte by using the redox current value. The biosensor after having extracted the value of concentration of total haemoglobin in the blood sample displays the value.

In another aspect of the present invention NaOH is used as a receptor to determine myoglobin content in human blood sample. The aforementioned receptors are used with this biological sample along with the steps as described above, to determine the myoglobin content. The biosensor thus used is advantageously provided with an electrode configuration as shown FIG. 8 (a).

Under alkaline conditions, myoglobin can be converted into alkaline hematin by separation of globin part. Hematin is the oxidized form of heme prosthetic group in haemoglobin structure. Hematin is relatively small molecule and can communicate with electrode surface more easily than haemoglobin molecule. Hematin gives the reduction peak in cyclic voltammetry as shown in FIG. 12. Hematin shows the good reduction peak can be use for electrochemical detection of myoglobin in human blood plasma.

Here it should be noted that the physiological concentration of myoglobin is very low in comparison to haemoglobin in human blood so the dimer formation is not evident in the detection of myoglobin.

The reduction current response of alkaline hematin based electrochemical detection of myoglobin is linear and this is due to the fact that the concentration of myoglobin is very low in blood as compared to the haemoglobin and we get the linear response of redox current with the myoglobin concentration.

The measured redox current is matched with the stored redox current values and the matching myoglobin concentration is secured and displayed by the biosensor. Alternately, using the redox current value can also use the linear-fit equation to compute the concentration of bioanalyte. The biosensor after having extracted the value of concentration of myoglobin in the blood sample displays the value.

Accordingly, the method of the present invention quantitatively and accurately measures concentrations of haemoglobin bioanalyte and its complexes in a blood sample. In this method a redox current is applied to the electrochemically active device having the electrode member, which is connected to the pair of conductive tracks. The desired blood sample having haemoglobin analyte and its complexes is permitted to contact with the lysing agent of the two-electrode member. Upon contact, the non-electrochemically active heamoglobin bioanalyte of the blood sample and its complexes are released from red blood cells (RBCs). The released non-electrochemically active heamoglobin bioanalyte and its complexes into corresponding electrochemically active heamoglobin bioanalyte and its complexes by the receptor that is integrated with the receptor-membrane. The concentrations of electrochemically active haemoglobin and its complexes are determined, by measuring a corresponding redox current and linearly matching it to concentrations of haemoglobin and its complexes.

In the method of the present invention, the reduced volume of blood sample is in the range of 1-300 microlitres (μL).

The subject matter of the invention is now illustrated in the form of the following examples. These examples are provided for purpose of illustration and shall not be construed as limiting the scope of the invention.

Example 1: Determination of Blood Haemoglobin Concentration and Corresponding Reduction Current Using Pyridine and NaOH as a Receptor 1.5 ml whole blood is lysed with 4 ml cold deionized (DI) water. 2 ml of 1% NaOH is added in this lysed solution to convert the Haemoglobin content into hematin. 1.5 ml of pyridine is added in hematin solution to convert it into pyridine hemichrome. From this master solution, different concentration of haemoglobin solutions are prepared by appropriate dilution of the pyridine hemichrome solution. Final volume of 300 μL is used for testing.

Figure 21A:
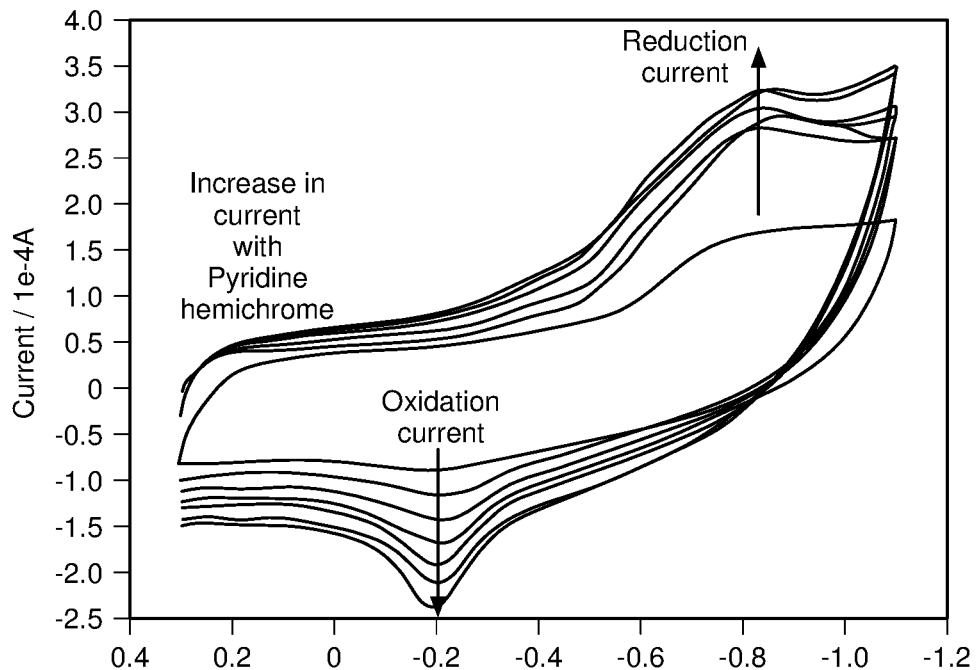
FIG. 21(a) is a cyclic voltammogram of haemoglobin after its conversion into pyridine hemichromes and FIG. 21(b) is plot of change in oxidation current Vs haemoglobin concentration.

A desired volume of the blood sample is taken and dispensed on the electrode of the biosensor device and the corresponding cyclic voltammogram is obtained by values using the CHI Electrochemical workstation using a potential window variation from 0.4 V to −1.2 V with scan rate of 0.6 V/sec., as shown in FIG. 21(a).

Figure 21B:
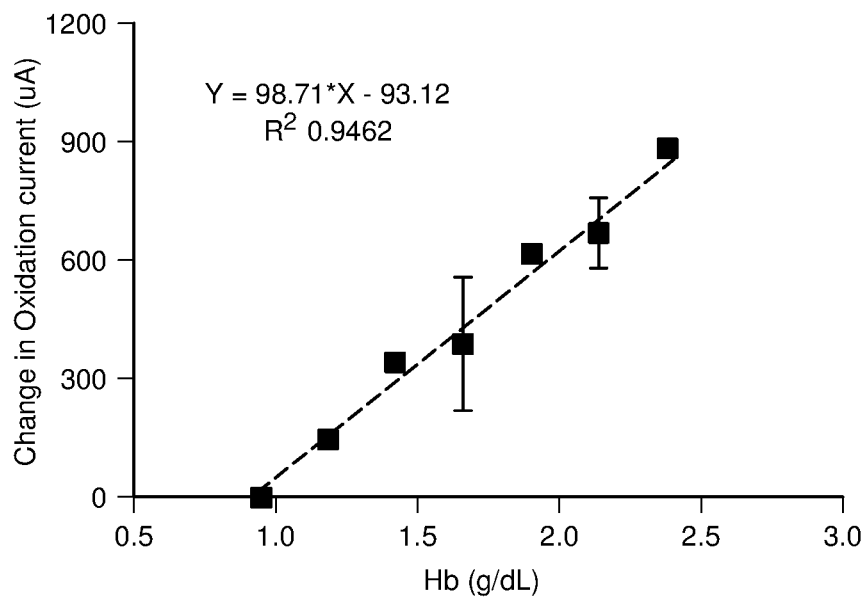

The cold DI water lyses the RBCs in the blood sample and releases the Hb molecule. NaOH denatures the haemoglobin molecule and separate the hemin and globin portions. Pyridine then converts hemin into pyridine hemichrome, which is an electrochemically active molecule. Pyridine hemichrome thereby demonstrates a linear increase in peak redox current with haemoglobin concentration as shown in FIGS. 21(a) and 21(b). If the concentration of haemoglobin in blood sample is increased, the formation of hemin is also increased, thereby increasing the pyridine hemichrome concentration on the electrodes, resulting in the increase in peak redox current.

The values of concentrations of the haemoglobin (g/dL) along with corresponding oxidation current values (μA) are recorded and tabulated as shown in Table 1.

Table 1 is prepared from linear fit equation as given below, which is derived from the repeatability data plots:

$$y = -10.37x - 23.68$$

In the above equation "y" represents the redox current value and "x" represents the concentration of analyte.

TABLE 1

| Hb Concentration (g/dL) | Oxidation current (µA) |
|---|---|
| 0.96 | 81 |
| 1.2 | 104 |
| 1.44 | 134 |
| 1.68 | 116 |
| 1.92 | 188 |
| 2.16 | 199 |
| 2.4 | 232 |

TABLE 2

| Hb Concentration (g/dL) | Oxidation current (µA) |
|---|---|
| 4 | 38 |
| 8 | 208 |
| 12 | 391 |
| 17 | 674 |
| 21 | 788 |
| 25 | 958 |

Example 2: Measurement of Haemoglobin with Pyridine and NaOH Receptor

A sample volume of pyridine hemichrome of 300 µL is placed on the electrode then the peak reduction current value is noted from cyclic voltammogram specifying a potential window from 0.4V to −1.2V in CHI Electrochemical workstation. The value of peak reduction current is measured as 238 µA. This current value is looked in the Table 1 and the corresponding concentration of haemoglobin is retrieved as 2.4 g/dL.

Example 3: Determination of Blood Haemoglobin Concentration for Physiological Range and Corresponding Reduction Current Using Pyridine and NaOH as a Receptor 1.5 ml whole blood is lysed with 4 ml cold DI water. 2 ml of 1% NaOH is added in this lysed solution to convert the haemoglobin content into hematin. The solid bovine hemin is added in this solution to further increase the hematin content for physiological range. Then 1.5 ml of pyridine is added to hematin solution, to convert it into pyridine hemichrome. From this master solution, different concentrations of haemoglobin solutions are prepared by appropriate dilution of the pyridine hemichrome solution. Final volume of 300 µL is used for testing.

Figure 22A:
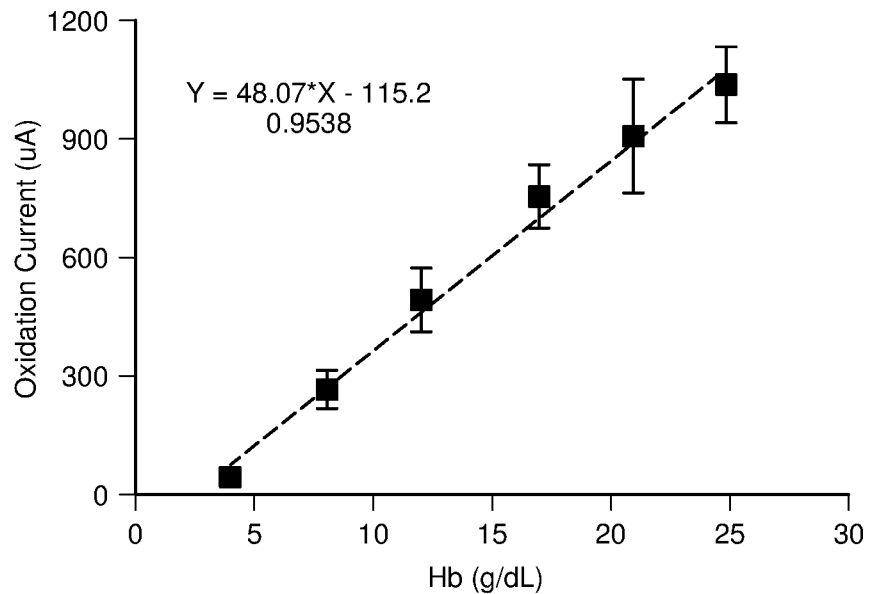
FIG. 22(a) is a plot depicting oxidation current Vs haemoglobin for a pathological range of haemoglobin and FIG. 22(b) is plot depicting change in oxidation current Vs haemoglobin for pathological range of haemoglobin.

A desired volume of the blood sample is taken and dispensed on the electrode of the biosensor device and the corresponding cyclic voltammogram is obtained by values using the CHI Electrochemical workstation using the potential window varying from 0.4 V to −1.2 V, with a scan rate of 0.6 V/sec, as shown in FIG. 22(a).

Figure 22B:
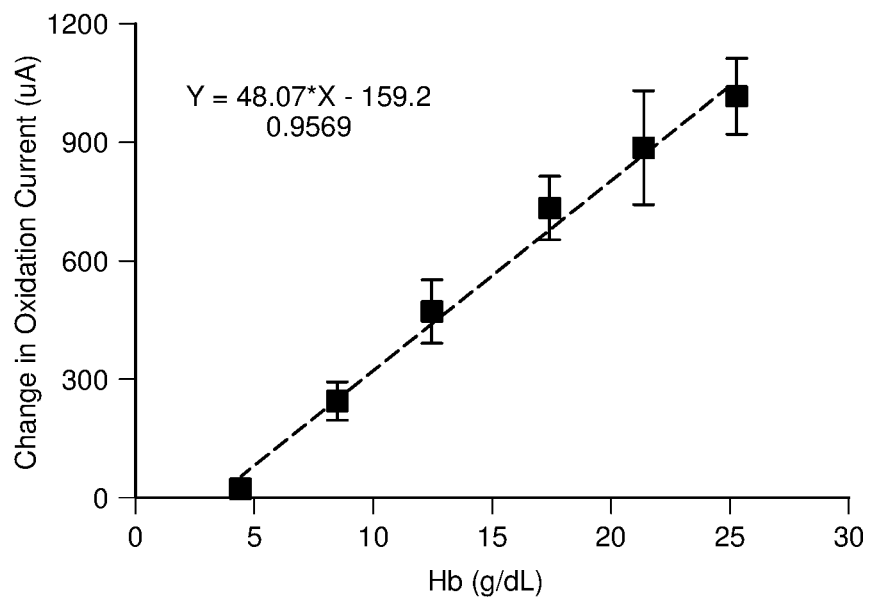

The cold deionised water (DI) lyses the RBCs in the blood sample and release the Hb molecule. NaOH denatures the haemoglobin molecule and separates hemin from globin portion. Pyridine then converts the hemin into pyridine hemichrome, which is an electrochemically active molecule. Pyridine hemichrome thereby demonstrates a linear increase in peak redox current with haemoglobin concentration as shown in FIG. 22(a) and FIG. 22(b). If the concentration of haemoglobin in blood sample is increased then more hemin will form thereby increasing the pyridine hemichrome concentration on the electrode resulting in the increase in peak redox current.

The values of concentrations of the haemoglobin (g/dL) along with corresponding oxidation current values (µA) are recorded and tabulated as shown in Table 2. Table 2 is prepared from linear fit equation as given below, which is derived from the repeatability data plots:

$$y=45.43-151.39$$

In the above equation "y" represents the redox current value and "x" represents the concentration of analyte.

Example 4: Measurement of Haemoglobin for Physiological Range with Pyridine and NaOH Receptor A sample volume of pyridine hemichrome of 300 µL is placed on the electrode then the peak reduction current value is noted from cyclic voltammogram specifying a potential window from 0.4V to −1.2V in CHI Electrochemical workstation. The value of peak oxidation current is 1014 µA. This current value is searched in the Table 1 and the corresponding concentration of haemoglobin is obtained is 25 g/dL.

Example 5: Determination of Blood Haemoglobin Concentration for Physiological Range and Corresponding Reduction Current Using Imidazole as a Receptor Sodium Dodecyl Sulfate (SDS) as Lysing Agent 5 gm of Imidazole, 200 mg SDS dissolved in 10 ml of DI water then a drop of 100 µL of this solution is dispersed on a piece of filter paper membrane and dried for 24 hours at room temperature. This membrane is arranged on top of the patterned electrodes.

Figure 23A:
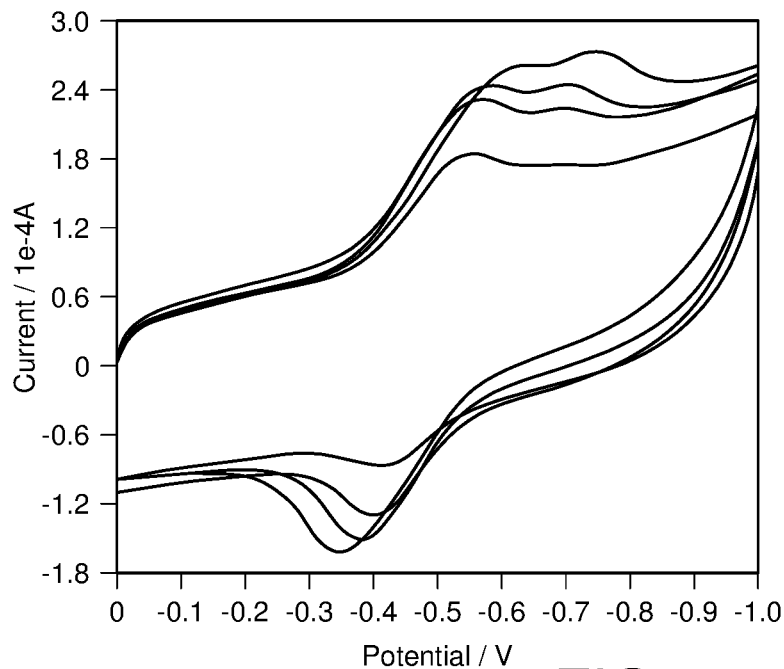
FIG. 23(a) is a cyclic voltammogram of haemoglobin subsequent to its conversion into imidazole-methaemoglobin complex and FIG. 23(b) is a plot of oxidation current Vs haemoglobin.

A 300 µL volume of the blood sample is taken and dispensed on the electrode of the biosensor device and the corresponding cyclic voltammogram is obtained by values using the CHI Electrochemical workstation using the potential window varies from 0 V to −1.0 V with scan rate of 0.6 V/sec, as shown in FIG. 23(a).

Figure 23B:
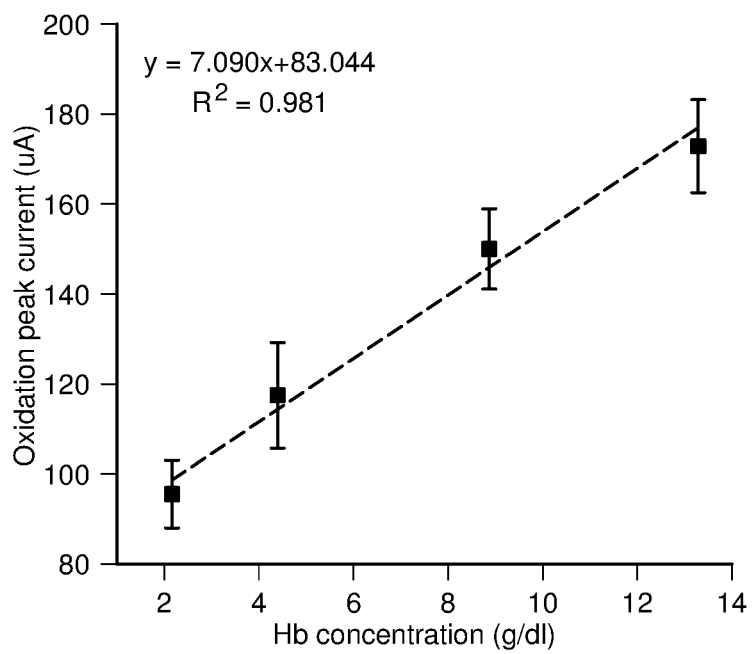

The sodium dodecyl sulphate (SDS) lyses the RBCs and converts the haemoglobin molecules into oxidized form, methaemoglobin in the blood sample. Imidazole forms the electrochemically active imidazole-methaemoglobin complex. The amount of Imidazole-methaemoglobin complex is higher for higher haemoglobin concentration, thereby demonstrating a linear increase in peak redox current with Haemoglobin concentration as shown in FIG. 23(a) and FIG. 23(b). If the concentration of haemoglobin in blood sample is increased then more methaemoglobin is formed thereby increasing the imidazole-methaemoglobin complex concentration on the electrode resulting in the increase in peak redox current.

The values of concentrations of the haemoglobin (g/dL) along with corresponding oxidation current values (µA) are recorded and tabulated as shown in Table 3. Table 3 is prepared from linear fit equation as given below, which is derived from the repeatability data plots:

$$y=7.090x+83.044$$

In the above equation "y" represents the redox current value and "x" represents the concentration of analyte.

TABLE 3

| Hb Concentration (g/dL) | Oxidation current (μA) |
|---|---|
| 2 | 95 |
| 4.5 | 118 |
| 9 | 150 |
| 13.4 | 174 |

Example 6: Measurement of Haemoglobin for Physiological Range with Imidazole as a Receptor and SDS as Lysing Agent A sample volume of whole blood of 300 μL is placed on the membrane fixed on top of the electrodes then the peak reduction current value is noted from cyclic voltammogram specifying a potential window from 0V to −1.0V in CHI Electrochemical workstation. The value of peak oxidation current is 144 μA. This current value is looked in the Table 1 and the corresponding concentration of haemoglobin thus obtained is 9 g/dL.

Example 7: Determination of Percentage Glycated Haemoglobin (% GHb) Concentration for Physiological Range and Corresponding Reduction Current Using Imidazole as a Receptor and SDS as Lysing Agent 1.5 gm of imidazole, 100 mg SDS dissolved in 10 ml of DI water then a drop of 100 μL of this solution is dispersed on a piece of filter paper membrane and dried for 24 hour at room temperature. This membrane is used for the detection of total haemoglobin in the whole blood sample.

1.5 gm of Imidazole, 100 mg SDS and 310 mg aminophenylboronic acid (APBA) are dissolved in 10 ml of DI water then a drop of 100 μL of this solution is dispersed on a piece of filter paper membrane and allowed to dry for about 24 hours at room temperature. This membrane is used for the detection of haemoglobin content in the whole blood sample without glycated haemoglobin content.

Figure 24:
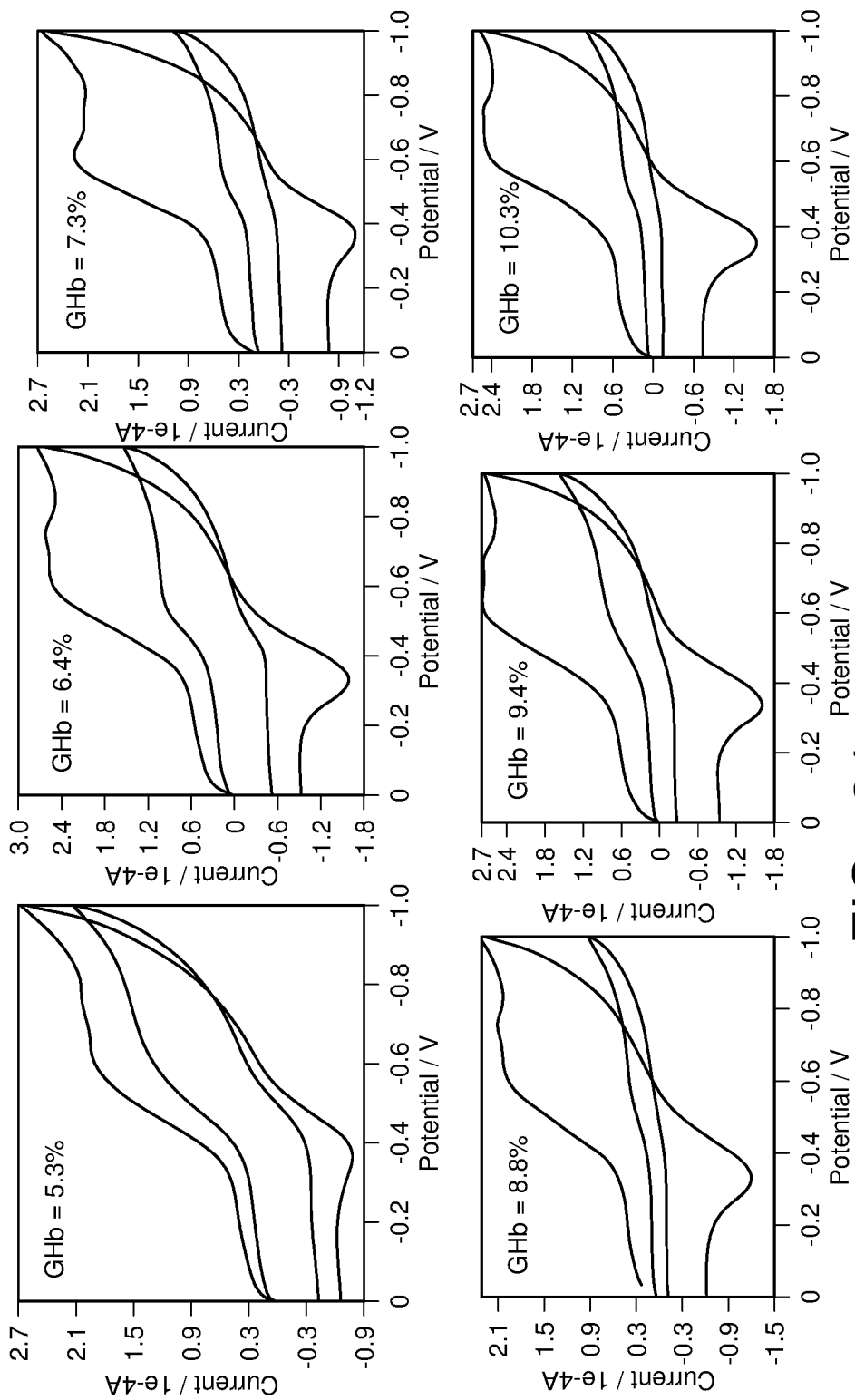
FIG. 24 is a cyclic voltammograms of total haemoglobin and haemoglobin without glycated Hb.

A 300 μL volume of the blood sample is taken and dispensed on the membranes fixed on top of the two set of three electrodes of the biosensor device and the corresponding cyclic voltammogram is obtained by values using the CHI Electrochemical workstation using the potential window varies from 0 V to −1.0 V with scan rate of 0.6 V/sec, as shown in FIG. 24.

The sodium dodecyl sulphate (SDS) lyses the RBCs and converts the Haemoglobin molecules into oxidized form, methaemoglobin in the blood sample. Imidazole forms the electrochemically active Imidazole-methaemoglobin complex. Imidazole-methaemoglobin complex thereby demonstrating a linear increase in peak redox current with Haemoglobin concentration as shown in FIG. 24. If the concentration of haemoglobin in blood sample is increased then more methaemoglobin will form thereby increasing the Imidazole-methaemoglobin complex concentration on the electrode resulting in the increase in peak redox current.

Figure 25:
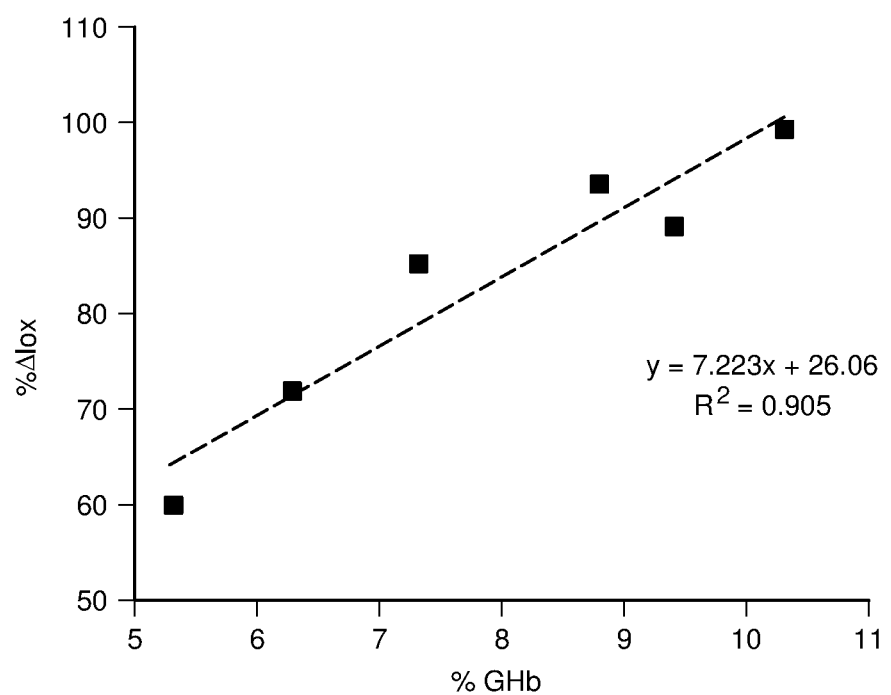
FIG. 25 is a plot depicting % glycated haemoglobin Vs oxidation current.

The second membrane is treated with aminophenylboronic acid (APBA) to filter the glycated haemoglobin content in the blood sample and a haemoglobin signal without the glycated Haemoglobin content is obtained as shown in FIG. 25.

The percentage glycated haemoglobin is proportional to percentage change in oxidation current with and without the glycated haemoglobin component, calculated by using the following formula:

$$\% \Delta I_{ox} = \frac{(Iox - Iox\_APBA) * 100}{(Iox)}$$

Where ΔIox is percentage change in current, I-ox is the oxidation current of total haemoglobin and I-ox_APBA is the oxidation current of haemoglobin in the absence of glycated haemoglobin component.

The values of concentrations of the percent glycated haemoglobin along with corresponding percentage change in oxidation current are recorded and tabulated as shown in Table 4.

Table 4 is prepared from linear fit equation as given below, which is derived from the repeatability data plots:

$$y=7.2233x+26.064$$

In the above equation "y" represents the redox current value and "x" represents the concentration of analyte.

TABLE 4

| % GHb | Percentage change in Oxidation current (%) |
|---|---|
| 5.3 | 60 |
| 6.3 | 71.875 |
| 7.3 | 85.10638298 |
| 8.8 | 93.65079365 |
| 9.4 | 89.02439024 |
| 10.3 | 99.11392405 |

Example 8: Measurement of Percent Glycated Haemoglobin for Physiological Range with Imidazole as a Receptor and SDS as Lysing Agent A sample volume of whole blood of 300 μL is placed on the membranes fixed on top of the two sets of three electrodes then the peak reduction current value is noted from cyclic voltammogram specifying a potential window from 0V to −1.0V in CHI Electrochemical workstation. The value of peak oxidation current for total haemoglobin blood sample is 80 μA while peak oxidation current without glycated haemoglobin component is 32 μA. The % GHb is calculated as follows:

$$\% I_{OX} = \frac{(80 - 32) * 100}{(90)} = 60\%$$

This current value is looked in the Table 4 and the corresponding % GHb thus obtained is 5.3.

Example 9: Determination of Myoglobin Concentration for Physiological Range and Corresponding Redox Current Using NaOH as a Receptor The standard solution of Sigma myoglobin is prepared in phosphate buffer saline. 1% NaOH solution is added in myoglobin solution. NaOH breaks the myoglobin structure and free alkaline hematin is released.

The peak reduction current linearly depends on the concentration of myoglobin concentration. Therefore, an increased quantity of myoglobin in the sample increases the quantity of alkaline hematin.

Figure 26:
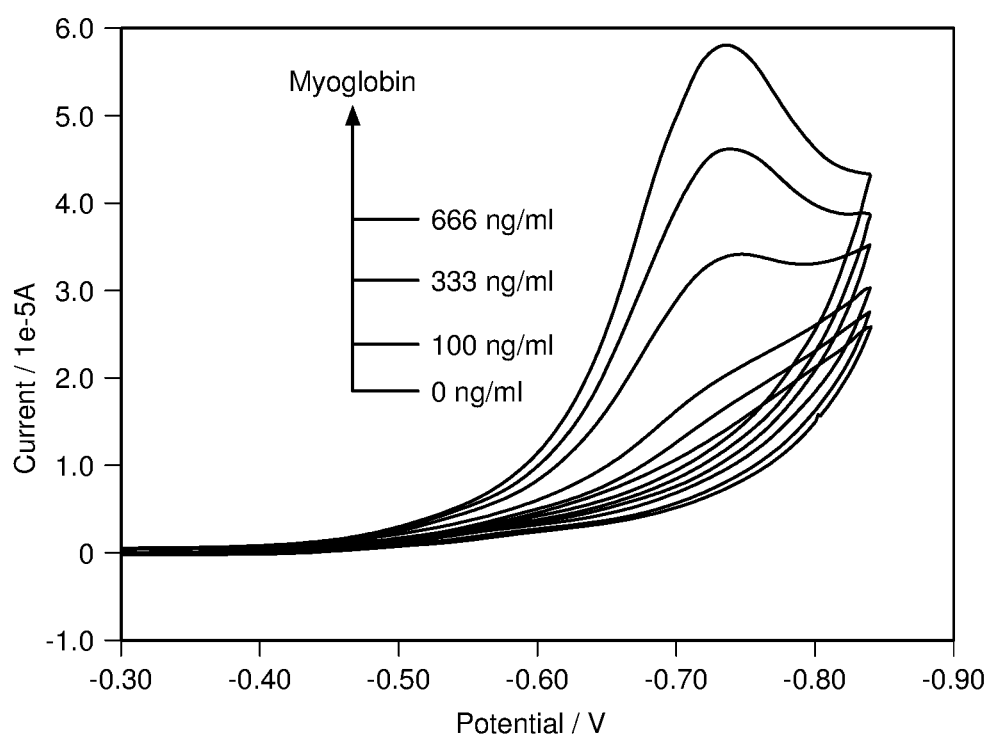
FIG. 26 is a cyclic voltammogram of myoglobin with different concentrations.

A 300 μL of myoglobin sample is dispensed on the electrode of the biosensor device and the corresponding cyclic voltammogram is obtained by values using the CHI Electrochemical workstation using the potential window varies from −0.30 V to −0.9 V with scan rate of 0.1 V/sec, as shown in FIG. 26.

Figure 27:
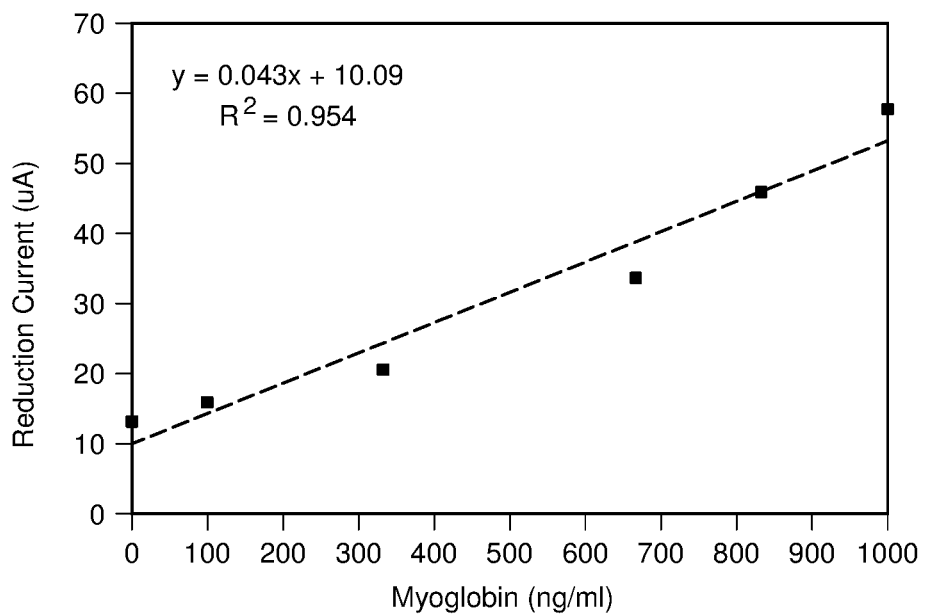
FIG. 27 is a plot of redox current Vs myoglobin concentration.

The peak reduction current is linearly dependent on the myoglobin concentration, as shown in FIG. 27

The values of concentrations of the myoglobin (ng/ml) along with corresponding reduction current values (μA) are recorded and tabulated as shown in Table 5.

Table 5 is prepared from linear fit equation as given below, which is derived from the repeatability data plots:

$$y=0.0432x+10.096$$

In the above equation "y" represents the redox current value and "x" represents the concentration of analyte.

TABLE 5

| Myoglobin (ng/ml) | Reduction current (μA) |
| --- | --- |
| 10 | 13 |
| 100 | 16 |
| 333 | 20.5 |
| 666 | 33.8 |
| 833 | 46 |
| 1000 | 57.8 |

Example 10: Measurement of Myoglobin for Physiological Range with NaOH as A Receptor A sample volume of whole blood of 300 μL is placed on the top of the electrode then the peak reduction current value is noted from cyclic voltammogram specifying a potential window from −0.3V to −0.9 in CHI Electrochemical workstation. The value of peak oxidation current is 46 μA. This current value is searched in the Table 1 and the corresponding concentration of myoglobin is thus obtained as 833 ng/ml.

ADVANTAGES OF THE PRESENT INVENTION

In the present invention non-enzymatic and non-antibody based receptors are used in conjunction with electrodes, for quantitative measurement bioanalytes viz., haemoglobin (Hb), glycated haemoglobin (GHb), methaemoglobin (MetHb) and myoglobin, in blood samples The present invention adopts a method of converting human haemoglobin and its complexes into electrochemically active substance for the electrochemical detection of bioanalytes related to human haemoglobin.

In the quantitative measurement of bioanalytes of the present invention a minimal invasive technique where a reduced volume of sample volume is used.

It is also understood that the following claims are intended to cover all the generic and specific features of the invention herein described and all statements of the scope of the invention, which as a matter of language might be said to fall there between.

We claim:

1. An electrochemically active device for collecting and retaining a blood sample, comprising:
   (i) at least a pair of conductive tracks disposed on a substrate;
   (ii) at least one electrode member comprising at least two electrodes, wherein said at least two electrodes are connected to said at least pair of conductive tracks, wherein said at least two electrodes are each carbon, glassy carbon, or graphite;
   (iii) a lysing membrane comprising at least one lysing agent and configured to receive a blood sample and to release a bioanalyte comprising non-electrochemically active hemoglobin or a complex thereof, from said blood sample;
   (iv) an integral-receptor membrane disposed between said at least one electrode member and said lysing membrane, said integral-receptor membrane comprising a N-heterocyclic organic receptor, wherein the receptor is a compound selected from the group consisting of pyridine, pyridine HCl, hydroxypyridine, cyanopyridine, imidazole, pyrazole, indole, pyrimidine and purine, wherein said receptor is configured to form a coordinated complex with said bioanalyte, wherein the coordinated complex is an electrochemically active receptor-hemichrome, and is configured to provide a reversible redox current peak on application of redox potential to the at least two electrodes.

2. The device as claimed in claim 1, wherein said substrate is a polymer or a paper.

3. The device as claimed in claim 1, wherein the at least two electrodes comprise three electrodes disposed on said substrate.

4. The device as claimed in claim 1, comprising a plurality of electrode members comprising two electrodes disposed on said substrate.

5. The device as claimed in claim 1, comprising a plurality of electrode members comprising three electrodes disposed on said substrate.

6. The device as claimed in claim 1, wherein said at least two electrodes are patterned electrodes.

7. The device as claimed in claim 1, wherein said integral-receptor-membrane and said lysing membrane comprise a polymer, cellulose, nitrocellulose, nylon, cotton fabric or paper.

8. The device as claimed in claim 1, wherein said lysing agent is selected from the group consisting of diocetyl sodium sulfosuccinate, sodium dodecyl benzene sulphonate, lauryl dimethylamine oxide, octylphenoxy poly ethoxy ethanol, potassium ferricyanide, sodium lauryl sulfate, lithium dodecyl sulfate, sodium nitrite, cetyletrymethyl ammonium bromide, sodium dodecyl sulfate, sodium deoxychelate, N-lauroylsarcosine, didodecyldimethylammonium bromide, octylphenol ethylene oxide condensate and hydrochloric acid.

9. The device as claimed in claim 1, wherein said lysing agent is combined with an inorganic substance.

10. The device as claimed in claim 1, wherein said bioanalyte is hemoglobin (Hb), glycated hemoglobin (GHb), methemoglobin (MetHb) or myoglobin.

11. The device as claimed in claim 10, wherein a glycated hemoglobin membrane is disposed below said lysing membrane and on said at least one electrode member having said integral-receptor-membrane and treated with a boronate affinity agent selected from the group consisting of boronic acids, phenyl boronic acid (PBA), and aminophenylboronic acid (APBA).

12. The device as claimed in claim 1, wherein said device is disposed in a housing, wherein said housing is a cartridge or a cassette.

13. A system comprising an electrochemically active device, and a holder for holding the electrochemically active device with a blood sample, said system comprising:

(i) a device detection and signal conditioning means disposed in a housing;
(ii) a USB connector disposed at one end of said housing and an electrically conductive port disposed at the other end of said housing; and
(iii) an electrochemically active device for collecting and retaining a blood sample connected to said holder through said electrically conducting port, wherein said electrochemically active device comprises:
   (a) at least a pair of conductive tracks disposed on a substrate, at least one electrode member comprising at least two electrodes; wherein said at least two electrodes are each carbon, glassy carbon, or graphite;
   (b) a lysing membrane comprising a lysing agent connected to said at least pair of conductive tracks and configured to receive a blood sample and to release non-electrochemically active bioanalyte comprising hemoglobin or a complex thereof, from said blood sample; and
   (c) an integral-receptor membrane disposed between said at least one electrode member and said lysing membrane, said integral-receptor membrane comprising a N-heterocyclic organic receptor, wherein the receptor is a compound selected from the group consisting of pyridine, pyridine HCl, hydroxypyridine, cyanopyridine, imidazole, pyrazole, indole, pyrimidine and purine, wherein said receptor is configured to form an electrochemically active receptor-hemichrome from said bioanalyte, and is configured to provide a reversible redox current peak on application of redox potential to the at least two electrodes.

14. The system as claimed in claim 13, wherein a glycated hemoglobin membrane is disposed below said lysing membrane and on said at least one electrode member having said integral-receptor-membrane and treated with a boron affinity agent, selected from the group consisting of boronic acids, phenyl boronic acid (PBA), and aminophenylboronic acid (APBA).

15. A point-of-care biosensor for measuring a concentration of a bioanalyte in a blood sample, said biosensor comprising:
(i) a housing with a display member and an electrically conducting port;
(ii) an electrochemically active device for collecting and retaining a blood sample connected to said holder through said electrically conducting port, said device comprising:
   (a) at least a pair of conductive tracks disposed on a substrate, at least one electrode member comprising at least two electrodes, wherein said at least two electrodes are each carbon, glassy carbon, or graphite;
   (b) a lysing membrane comprising a lysing agent connected to said at least pair of conductive tracks and configured to receive a blood sample and release non-electrochemically active bioanalyte comprising hemoglobin or a complex thereof from said blood sample; and
   (c) an integral-receptor membrane disposed between said at least one electrode member and said lysing membrane, said integral-receptor membrane comprising a N-heterocyclic organic receptor, wherein the receptor is a compound selected from the group consisting of pyridine, pyridine HCl, hydroxypyridine, cyanopyridine, imidazole, pyrazole, indole, pyrimidine and purine, said receptor configured to form an electrochemically active receptor-hemichrome from said bioanalyte and configured to provide a reversible redox current peak on application of redox potential to the at least two electrodes; and
(iii) a digital controller disposed in said housing and configured to apply a redox potential and measure redox current from said device, retrieve and display concentration levels of hemoglobin and its complexes by linearly matching the concentrations of hemoglobin and its complexes thereof.

16. The point-of-care biosensor as claimed in claim 15, wherein a glycated hemoglobin membrane is disposed below said lysing membrane and on said at least one electrode member having said integral-receptor-membrane and treated with a boron affinity agent selected from the group consisting of boronic acids, phenyl boronic acid (PBA), and aminophenylboronic acid (APBA).

17. The point-of-care biosensor, as claimed in claim 15, wherein a database member with stored standard concentration values for hemoglobin bioanalyte concentrations and complexes thereof in blood samples along with reciprocal redox currents is connected to said digital controller.

18. A method for measuring concentrations of hemoglobin bioanalyte and complexes thereof in a blood sample, comprising the steps of:
(i) receiving a blood sample with hemoglobin bioanalyte and complexes thereof, having red blood cells (RBCs) on the device according to claim 1;
(ii) releasing non-electro chemically active hemoglobin bioanalyte and complexes thereof from red blood cells (RBCs) of said blood sample;
(iii) forming an electrochemically active receptor-hemichrome from said non-electrochemically active hemoglobin bioanalyte and complexes thereof;
(iv) applying a redox voltage to said at least one electrode member and determining the concentration of said electrochemically active receptor-hemichrome, by measuring a corresponding redox current; and
(v) determining the concentration of hemoglobin and complexes thereof in said blood sample, by linearly matching the corresponding redox current to concentrations of hemoglobin and complexes thereof.

19. The method as claimed in claim 18, wherein the blood sample has a volume is in the range of 1-300 microliters (µL).

20. The method as claimed in claim 18, wherein said non-electrochemically active hemoglobin bioanalyte and complexes thereof comprises hemoglobin (Hb), glycated hemoglobin (GHb), methemoglobin (MetHb) or myoglobin.

21. The method as claimed in claim 20, wherein
the device comprises at least two two-electrode members, wherein one of said at least two two-electrode members is arranged with a glycated hemoglobin membrane to filter glycated hemoglobin from said blood sample, wherein one of said at least two two-electrode members measures the concentration of total hemoglobin by measuring total redox current and another of said at least two two-electrode members measures concentration of non-glycated hemoglobin by measuring non-glycated redox current due to the filtration of glycated hemoglobin by the glycated hemoglobin membrane;
obtaining the percentage glycated redox current by subtracting said non-glycated redox current from said total redox current, and dividing the resultant difference current by said total redox current to get percentage glycated redox current; and determining percentage glycated hemoglobin by linearly matching the percentage glycated redox current with the values of percentage glycated hemoglobin.

* * * * *